(12) United States Patent
Elsner

(10) Patent No.: US 11,375,891 B1
(45) Date of Patent: Jul. 5, 2022

(54) METHODS, SYSTEMS, AND DEVICES FOR VISION TESTING

(71) Applicant: The Trustees of Indiana University, Bloomington, IN (US)

(72) Inventor: Ann E. Elsner, Bloomington, IN (US)

(73) Assignee: The Trustees of Indiana University, Bloomington, IN (US)

( * ) Notice: Subject to any disclaimer, the term of this patent is extended or adjusted under 35 U.S.C. 154(b) by 0 days.

(21) Appl. No.: 17/554,703

(22) Filed: Dec. 17, 2021

(51) Int. Cl.
*A61B 3/10* (2006.01)
*A61B 3/14* (2006.01)
*A61B 3/00* (2006.01)
*A61B 3/028* (2006.01)

(52) U.S. Cl.
CPC .......... *A61B 3/1015* (2013.01); *A61B 3/0008* (2013.01); *A61B 3/0025* (2013.01); *A61B 3/028* (2013.01); *A61B 3/101* (2013.01); *A61B 3/1025* (2013.01)

(58) Field of Classification Search
CPC .... A61B 3/10; A61B 3/00; A61B 3/14; A61B 3/02
USPC ....... 351/221, 200, 205, 209, 210, 206, 222, 351/246
See application file for complete search history.

(56) References Cited

U.S. PATENT DOCUMENTS

2003/0223037 A1\* 12/2003 Chernyak ............... G06T 7/337
351/209
2012/0038885 A1\* 2/2012 Cense ................... A61B 3/102
356/492
2019/0282082 A1\* 9/2019 Wahl ...................... A61B 3/024

\* cited by examiner

*Primary Examiner* — Dawayne Pinkney
(74) *Attorney, Agent, or Firm* — Taft Stettinius & Hollister LLP

(57) ABSTRACT

Methods, systems, and devices to improve the assessment of visual function and overcoming limitations of current methods to identify the visual function that potentially could be reached by a given eye. Multiple eye tests including visual stimuli plus optical measurement components, and methods to combine the results, identify and quantify sources of decreased vision resulting from optical sources, such as a lens and cornea as distinguished from retinal sources. By identifying potentially correctable optical sources of decreased vision, and overcoming physiological limitations such as size of the eye's pupil, the visual benefits of treatment such as by cataract or corneal surgery are distinguished from retinal pathology that requires medical intervention. The devices and methods provide metrics that include an expected value of the visual function and sources of variability including both optical and neural components, to guide treatment and improve clinical trials.

26 Claims, 9 Drawing Sheets

METHODS, SYSTEMS, AND DEVICES FOR VISION TESTING

STATEMENT REGARDING FEDERALLY SPONSORED RESEARCH OR DEVELOPMENT

This invention was made with government support under EY030829 awarded by the National Institutes of Health. The Government has certain rights in the invention.

BACKGROUND OF THE INVENTION

Visual acuity and other visual functions guide the management of patients with retinal diseases and conditions. Such tests of visual function also serve as endpoints for clinical trials to investigate treatments. While printed and electronic charts to measure visual acuity or other visual functions are commonly used because they are standardized, easy to use, and can be widely distributed, they are inaccurate for the purpose of evaluating the status of the retina. Such charts fail to minimize or quantify factors that degrade eye performance due to optical factors such as stray light, poor transmission, and lack of sharp focus due to problems with the eye's tear film, cornea, or lens.

Additional optical factors include, but are not limited to, lack of an adequate refraction, particularly when the correction for refractive error is not contemporaneous with measurements using the visual function chart or is incorrect due to the plane of the retina at the target location being altered, such as by subretinal fluid. Further, methods using eye charts cannot control the size of the pupil, which varies greatly among individuals and with the pupils often being smaller at older ages, and therefore can strongly reduce the amount of light transmitted to the retina. When one or more sources of optical degradation are present, a common clinical remedy of providing a pinhole to minimize the angle over which light can enter the eye and the cross section of the pupil that can transmit light, can lead to even greater variation in light transmission. Methods using charts do not control or specify the fixation position of the eye that aligns the visual stimulus to the retina, leading to a lack of information about the area of retina that subserves the visual function measurement. Further, charts do not specify the stability of fixation that impacts vision when there is a lack of fixation stability.

Numerous optical devices provide a visual display with one or more design features to control for or specify information from these display features that factor into an assessment of eye function. For visual acuity closely related to retinal function, all of these display factors, including a high resolution display and a model to combine the information, are relevant to determining retinal function. Factors such as the exact stimulus and number of letters influence the performance on vision tests, including visual acuity tests. While potentially important to estimate reading ability, such tests may detract from the accuracy when evaluating the status of the retina. Models used to improve accuracy and test efficiency for visual acuity and other visual functions have included procedural details and stimulus parameters. These models, however, do not adequately minimize or specify the impact on central tendency and variability of the optical and performance factors on the measurements of visual function in the model. The measurement of the above non-retinal factors and a model are needed to specify the visual function of the retina and the potential vision that it might reach with treatment.

The present invention is intended to improve upon and resolve some of these known deficiencies within the relevant art.

SUMMARY OF THE INVENTION

The present invention relates to methods, systems, and devices designed for diagnostic use by eye care providers and researchers in clinical trials to more accurately specify the visual function of an eye and the potential for improvement with treatment. The methods, systems, and devices achieve simplicity of operation, patient comfort, and efficiency. The methods, systems, and devices are suitable for providing the broad range of information needed to specify the causes of decreased vision, which impact on treatment decisions. The systems has several subsystems that together provide improved accuracy and can be manufactured at significantly less cost or provide better accuracy and efficiency than systems that perform only some of the functions of the subsystem. The device and system can readily interface with modern computer technology to augment the database used in decision making or transmit information to an external database for decision making for treatment decisions.

The technology of the present disclosure provides devices and methods that are far more advanced than the typical wall chart or computer screen, which have accentuated problems especially related to the aging eye. Errors and variability are a direct result of these artifacts and cannot be overcome merely with software or algorithms, of which many have been proposed that address specific stimuli or optotype; algorithm for stimulus presentation; or testing factors such as patient fatigue, the criterion used by the patient, or cognitive deficits. See for instance U.S. Pat. No. 10,758,120 to Lesmes. The innovations of the present disclosure remedy many of these problems by combining one or more of the following features.

The present invention provides 1) an assessment of fixation location using video rate and near infrared retinal imaging that is invisible to the patient. The part of the retina used to fixate and to perform a visual function test is pinpointed. Without retinal imaging that is approximately video rate or faster, it is not possible to know the location of the visual stimulus with respect to the status of the retina, since the human eye moves frequently. Wall charts and computer screens do not document this relation. Thus, it is not known whether the portion of the retina that is being considered for treatment is in fact at the location that underlies the measured performance. With video rate retinal imaging, this location is determined. Further, without retinal imaging that is relatively fast with respect to eye movements, it is not possible to determine whether there is an instability of the eye, and whether the visual target is smeared across the retina or whether the eye is in position long enough to permit detection or recognition of a visual target. As used herein, video rate includes an image capture or display rate of at least 10 frames per second.

The extensive use of near infrared light as an illumination source to provide retinal images that visualize retinal landmarks and structures, in lieu of other wavelengths or color images, has been discussed extensively in Elsner, A. E., et al., Infrared Imaging of Sub-retinal Structures in the Human Ocular Fundus, Vision Res., Vol. 36, No. 1 (1996), pp. 191-205 ("Elsner et al., 1996"). Several implementations have been demonstrated by the inventor, A. E. Elsner. See for instance: Elsner, A. E., Burns, S. A., Hughes, G. W., & Webb, R. H. (1992). Reflectometry with a scanning laser ophthalmoscope. *Applied optics,* 31(19), 3697-3710. ("Elsner et all, 1992") and Elsner, A. E., et al., Multiply scattered light tomography: Vertical cavity surface emitting laser array used for imaging subretinal structures, Lasers and Light in Ophthalmology, 1998 ("Elsner et al., 1998a").

While each implementation has unique features, high quality images of the retina that have been obtained by means of numerous methods are suitable for combining with the projection of visual stimuli onto the retina, while providing information about retinal status in eye disease, e.g. scanning with a point of light and detecting the light returning from the retina one location at a time and in synchrony: Hartnett, M. E. and Elsner, A. E., Characteristics of Exudative Age-related Macular Degeneration Determined In Vivo with Confocal and Indirect Infrared Imaging, Ophthalmology, Vol. 103, No. 1 (January 1996), pp. 58-71 ("Hartnett et al., 1996a"); and Hartnett, M. E., et al., Deep Retinal Vascular Anomalous Complexes in Advanced Age-related Macular Degeneration, Ophthalmology, Vol. 103, No. 12 (December 1996), pp. 2042-2053 (Hartnett et all, 1996b"). The locations on the patient's retina of the fixation and of the visual stimuli are well-visualized by the inventor A. E. Elsner and colleagues: Remky, A., Eisner, A. E., Morandi, A. J., Beausencourt, E., & Trempe, C. L. (2001). Blue-on-yellow perimetry with a scanning laser ophthalmoscope: small alterations in the central macula with aging. *Journal of the Optical Society of America. A, Optics, image science, and vision,* 18(7), 1425-1436; ("Remky et al., 2001"); Remky, A., & Elsner, A. E. (2005). Blue on yellow perimetry with scanning laser ophthalmoscopy in patients with age related macular disease. *The British journal of ophthalmology,* 89(4), 464-469 ("Remky et al., 2005"); and Moraes, L., Elsner, A. E., Kunze, C., Suzuki, H., Nehemy, M. B., Soriano, D. S., & Kara-José, N. (2007). Avaliação da perimetria macular em pacientes com degeneração macular relacionada à idade por meio do oftalmoscópio de rastreamento a laser—Evaluation of macular perimetry in patients with age-related macular degeneration using the scanning laser ophthalmoscope. *Arquivos brasileiros de oftalmologia,* 70(5), 844-850 ("Moraes et al., 2007").

Analogous methods have been used by the inventor to image the retina using near infrared illumination consisting of a scanned strip of light and detection in synchrony with either a one dimensional or two dimensional array: See for instance U.S. Pat. Nos. 7,331,669, 7,831,106, 8,237,835, and 8,488,895. Near infrared images of the retina are combined, as described herein, with a visual display so that the locus of fixation and the location of the stimuli on the retina are clearly documented with the use of near infrared or long wavelength visible illumination, shown by Elsner, A. E., Petrig, B. L., Papay, J. A., Kollbaum, E. J., Clark, C. A., & Muller, M. S. (2013). Fixation stability and scotoma mapping for patients with low vision. *Optometry and vision science: official publication of the American Academy of Optometry,* 90(2), 164-173 ("Elsner et al., 2013") and Elsner, A. E., Papay, J. A., Johnston, K. D., Sawides, L., de Castro, A., King, B. J., Jones, D. W., Clark, C. A., Gast, T. J., & Burns, S. A. ("Elsner et al., 2020), Cones in ageing and harsh environments: the neural economy hypothesis. *Ophthalmic & physiological optics: The Journal of the British College of Ophthalmic Opticians (Optometrists)*, 40(2), 88-116 ("Elsner et al., 2020").

The present invention provides: 2) an assessment of fixation stability using the same video rate near infrared retinal imaging. The patient's eye movements are analyzed by aligning retinal images acquired over time.

The present invention 3) identifies the optical errors of a patient's eye and are not limited to sphere and cylinder, but includes other optical errors resulting from pathological conditions or aging conditions found in the cornea, lens, or pupil, collected by wavefront sensor measurement of the light returning from the retina. These errors result from wavefront aberrations that lead to complex sources of blur on the retina, making it difficult to determine if reduced visual acuity is due to retinal disease vs. anterior segment issues such as cataract or poor tear film. Increased age has long been known to increase these optical errors that blur visual stimuli on a patient's retina, with the blur not readily remedied by merely adding sphere or cylinder corrections, such as those found in spectacles. See for instance how age-related changes in monochromatic wave aberrations of the human eye can be measured as reported by McLellan, J. S., Marcos, S., & Burns, S. A. (2001); *Investigative ophthalmology & visual science,* 42(6), 1390-1395. The present disclosure therefore provides one or more embodiments including method and/or apparatuses that emphasizes improving the characterization of factors underlying the visual performance or function in the aging eye, which reduces the cost and improves the accuracy of analyzing eye conditions.

The present invention 4) provides an objective correction with adaptive optics during the measurement of visual function of the main optical errors of a patient's eye, which is not limited to sphere and cylinder, using the wavefront measurements discussed above in item 3 above. The present invention also provides an estimate of the accuracy of the measurements leading to the correction and the expected success of the correction. This enables visual function tests to be performed using a beam of directed light that is precisely focused onto the retina, which provides a better and more complete result than can be achieved with just the standard correction of sphere and cylinder, or the habitual refraction that is often significantly in error when there is retinal elevation as the result of exudative eye disease. This feature is in essence an autorefractor that includes more than just sphere and cylinder, and provides even greater accuracy in when used in combination with the other features that are not found in an autorefractor.

The optical correction necessary to provide correction of the higher order aberrations, and therefore to improve the measurement of visual functions that depended upon high contrast at high spatial resolution was not possible prior to the use of wavefront corrected imaging of the fundus by the author and colleagues, Burns, S. A., Marcos, S., Elsner, A. E., & Bara, S. (2002). Contrast improvement of confocal retinal imaging by use of phase-correcting plates. *Optics letters,* 27(6), 400-402. Previous instruments did provide a fundus image and visual stimuli but lacked adequate spatial resolution to test visual acuity, first shown by Timberlake and colleagues Timberlake, G. T., Mainster, M. A., Peli, E., Augliere, R. A., Essock, E. A., & Arend, L. E. (1986). Reading with a macular scotoma. I. Retinal location of scotoma and fixation area. *Investigative ophthalmology & visual science,* 27(7), 1137-1147.

In the above known prior methods for refractive correction beyond sphere and cylinder described and cited above, a wavefront measurement device has been used in combination with the retinal image. In an embodiment to reduce cost and complexity of components, it is possible to use information in the image to quantify the optical quality of the eye. This has been done to examine refractive error for the spherical component, Clark C A, Mueller M, Petrig B, Elsner A E, Refractive Error Across the Posterior Pole Using a Novel Retinal Imaging Technique. Association for Research in Vision and Ophthalmology, 1007/A570, 2010 ("Clark et al., 2010"); Clark C A, Elsner A E, Muller M S, Petrig B L. Peripheral Refraction Across The Posterior Pole Using Structured Illumination. ARVO Annual Meeting, Investigative Ophthalmology & Visual Science 52 (14), 2717-2717, 2011 ("Clark et al., 2011"); Elsner A E, Muller M S, Petrig B L, Papay J A, Christopher C A, Jovan A, Haggerty B P. Toward Low Cost Imaging: A Laser Scanning Digital Camera. Bio-Optics: Design and Application (BODA) 2011 paper: BWA1 ("Elsner et al., 2011").

In addition, information in the fundus image provides autofocus of a retinal camera. This technique is known as sensorless adaptive optics (AO) described in Burns, S. A., Elsner, A. E., Sapoznik, K. A., Warner, R. L., & Gast, T. J. (2019). Adaptive optics imaging of the human retina Progress in retinal and eye research, 68, 1-30 "(Burns et al., 2019"). In some cases, the retinal image does serve as a sensor. By injecting a spatial pattern such as black and white stripes into the illumination, there is improvement in the contrast of the fundus image, described in the above Clark references. Thus, there is in effect a sensor, i.e. the retinal image and computations. While projection of a pattern onto the retina has been accomplished with both point scanning and line scanning, there has not been use of wide field image and computations of wavefront errors based on a specific part of the retinal image that has a known spatial relation to fixation. The area on the retina to be corrected with the adaptive optics may or may not be located at the fovea or the fixation, i.e. visual stimuli are viewed eccentrically or when peripheral vision is being tested. The quality of this computation is a measure of the optical quality of the eye, and the results can be used in the variability and the assessment of potential visual performance. Repeated measurements quantify this optical quality, even with eye motion, based on computations of the fundus image after the correction with adaptive optics. The feedback loop would then consist of the fundus image, the computations from the image, and the adaptive optics. See for instance Clark, 2010; Clark, 2011; Elsner, 2011.

It is well-known that consideration of the factors of visual stimuli including retinal eccentricity, which is the distance from the fovea, and contrast can improve the sensitivity of visual function testing, along with the specific algorithm, Hahn, G. A., Messias, A., Mackeben, M., Dietz, K., Horwath, K., Hyvärinen, L., Leinonen, M., & Trauzettel-Klosinski, S. (2009). Parafoveal letter recognition at reduced contrast in normal aging and in patients with risk factors for AMD. *Graefe's archive for clinical and experimental ophthalmology—Albrecht von Graefes Archiv fur klinische und experimentelle Ophthalmologie,* 247(1), 43-51. The distance from the fovea of a visual stimulus is quantified by retinal imaging. Measurement of contrast of a visual stimulus projected through the optics of the eye and on the retina is improved by the use of wavefront measurement. To reduce cost and complexity, computations from the retinal image, with or without structured illumination, can also be used to provide information about the contrast of a visual stimulus on the retina. Another method to reduce cost and complexity is to use the visual display as the illumination for the wavefront sensor. With the limited sensitivity of current sensors at present, NIR illumination is preferred for simultaneous measurement of contrast of visual stimulation on the retina during visual function measurements because visible wavelength illumination would have to be so bright was to interfere with a visual function task. However, in one or more of the disclosed embodiments, the visual display is used as the illumination source for estimating wavefront error, using alternation of the visual stimuli that have wavelengths in the visible range and the measurement of contrast by either a wavefront sensor or the retinal imaging method. In one or more embodiments, light of wavelengths shorter than near infrared (NIR) are used. In another embodiment, temporal modulation of the illumination for the wavefront sensor or the retinal image can also be used to provide frequency-based detection schemes to improve the signal-to-noise ratio. In other embodiments, more complex schemes of homodyne and heterodyne detection, based on frequency are used to improve signal-to-noise ratio.

Outside of recent augmented reality (AR) and virtual reality (VR) devices, previous products that offered refractive correction beyond sphere and cylinder have found limited markets to date because the wavefront information and correction cannot be applied to ordinary spectacle lenses or contact lenses that do not tightly position the location of the pupil of the eye to the correction device. Expensive devices that include headsets, such as for AR or VR or laboratory devices can have positioning mechanisms, and intraocular lenses are able to utilize this (higher order refractive) information because of their positioning with respect to the pupil.

The present invention 5) projects a visual target onto the retina through a fixed size pupil of the instrument to reduce the enormous variability due to individual differences in the size of a patient's natural pupil, when compared with an ideal pupil size or based on the amount of light reaching the retina through the pupil.

Differences in pupil size lead to more or less light reaching the retina, as well as altering the optical throughput due to differences in the numerical aperture at the entrance pupil of the eye and differences in the depth of focus. This method of projection of the visual target is a well-known technique, used in a wide variety of applications, and in many versions of devices that provide both fundus imaging that gives a retinal image and projection of a visual stimulus, including both devices that incorporate the visual stimulus as part of the illumination with scanning a point. See the following references for additional information: Timberlake, G. T., Mainster, M. A., Peli, E., Augliere, R. A., Essock, E. A., & Arend, L. E. (1986). Reading with a macular scotoma. I. Retinal location of scotoma and fixation area. *Investigative ophthalmology & visual science,* 27(7), 1137-1147 or scanning a line Elsner et al., 2020 and with scanning a point and including correction of higher order optical aberrations Rossi, E. A., Weiser, P., Tarrant, J., & Roorda, A. (2007). Visual performance in emmetropia and low myopia after correction of high-order aberrations. *Journal of vision,* 7(8), 14 ("Rossi et al., 2007") to having the retinal image and visual stimuli provided by separate illumination channels when scanning a point to produce a retinal image, as in Remky et al., 2001; Remky et al, 2005; and Moraes et al., 2007, or when scanning a line to produce a retinal image (Elsner et al., 2013). Several embodiments have been described in the following: U.S. Pat. Nos. 7,331,669, 7,831, 106, 8,237,835, and 8,488,895.

The present invention 6) provides an analysis of the retinal images with confocal and multiply scattered light or adjusts the time difference or position difference between illumination and detection (temporal or spatial detection offset), i.e. modes of imaging, detailing the exact pathology at the point of fixation that is used by the patient in the vision test, clarifying the status of the retina at that location by use of confocal or multiply scattered light imaging and combinations of information from different imaging modes as described by U.S. Pat. Nos. 7,331,669, 7,831,106, 8,237,835, and 8,488,895. Additional examples of detection offset include, but are not limited to, the ratio at each location in the image of the intensity difference in each image to the sum at each location; the ratio at each location in the image of the intensity of the confocal image intensity to an image with a larger offset, and similar computations aggregating areas wider than a specific location or pixel. Infrared imaging with a scanning laser ophthalmoscope (SLO), the multiply scattered light tomographer, the laser scanning digital camera, and the digital light ophthalmoscope have been used to perform reflectometry techniques to view the eye rapidly and noninvasively. Initially implemented with scanning laser devices, infrared and near infrared imaging of sub-retinal structure in the ocular fundus has been able to reveal sub-retinal deposits, the optic nerve head, retinal vessels, choroidal vessels, fluid accumulation, hyperpigmentation, atrophy, and breaks in Bruch's membrane. Infrared light is absorbed less than visible light and may scatter over longer distances. With flood illumination, these features have not been observed with the same clarity or in lesser numbers. The relatively less absorption has advantages in that a minimum of light may be used as an illumination source. However, the reflected and scattered light must be separated in some manner, and the light used to accentuate the features of interest made available to the user.

The methods for detecting and localizing such features are described in the prior art of the inventor and colleagues: Elsner et al., 1996; 1998a; Elsner, A. E., et al., Foveal Cone Photopigment Distribution: Small Alterations Associated with Macular Pigment Distribution, Investigative Ophthalmology & Visual Science, Vol. 39, No. 12 (November 1998), pp. 2394-2404; Hartnett et al, 1996a; Hartnett, et al., 1996b; Remky et al.; 2005; and Elsner, et al., 2020, as examples. Specifically, when a retinal image acquired is only of the macula, centered on the fovea, the only features present in the normal eye with near infrared illumination are the retinal and choroidal blood vessels, and potentially superficial reflections, such as from the fovea. In a monochromatic image, any differences from these features in image intensity, beyond the noise inherent in any electronic signal, is interpreted as pathology. If the optic nerve head is also in the image, either due to a sufficiently large field of view or positioning of the eye with respect to the instrument to incorporate this feature, then intensity changes in the retina also define the position and condition of such a structure. It has been shown by Hartnett et al., 1996a; Elsner et al., 1996, and Miura, M., et al., Grading of Infrared Confocal Scanning Laser Tomography and Video Displays of Digitized Color Slides in Exudative Age-Related Macular Degeneration, Retina, Vol. 22, No. 3 (2002), pp. 300-308, that such monochrome images using infrared illumination are superior for the detection of certain features over methods using color photography.

The present invention further provides: 7) a novel system is for measuring potential vision that includes a combination of all the components 1 through 6 described above, using a unique statistical analysis. The present disclosure provides a metric with a measure of central tendency, for example the mean, plus the variability, for example the variance, and reporting of the significance of confounding reasons for reduced vision. For instance, reporting out of the wavefront errors shows how vision measurements are limited in a cataract. The unique statistical analysis combines the information from the variety of sources described above to place bounds on the expected performance. For example, to determine the potential vision that a specific eye could achieve with retinal treatment, there are bounds such as confidence limits derived from the central tendency (expected value) and variability, including optical errors, fixation data, and other data. Using the aberrations that are measured and determined to be correctable, the upper and lower bounds of the potential vision that can be achieved in a measurement like the widely used logarithm of the minimum angle of resolution (Log MAR) for characterization of visual acuity. A sample method includes, but is not limited to targets that are tumbling E's and a paradigm that includes four (4) possible directions for the E to point but only one patient response allowed (four alternative forced choice). The statistical analysis includes the determination of whether optical and neural, as well as other factors, are independent or whether they must be modelled as interacting.

A key tenet of the model includes the collection of data to determine whether the variables are independent and the overall variance is the sum of the variance of individual factors. Conversely, the model may require a function beyond simple addition of the variances of two or more variables that must be used to compute the expected visual function performance once the optical factors are corrected. Further, each of the variables may have a function more complex than a Gaussian distribution, and the variance may be distributed in a manner that is not symmetric around a mean value nor scaled linearly with the mean value. The combined variance is used to compute upper and lower confidence limits. These confidence limits, i.e. the bounds used to interpret a visual function test score, become broader or narrower, depending on the function that combines the variances for the component factors. The upper bound corresponds to the value that the visual function measurement must exceed for the retinal treatment to be considered a success, or to count as improvement in longitudinal measurements. The lower bound corresponds to the value that the visual function must exceed or be considered as not worsening on follow-up. These values may be related to current metrics, such as lines of vision gained or lost, that lack the important assessment of the influence of optical, fixation stability, or other factors.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
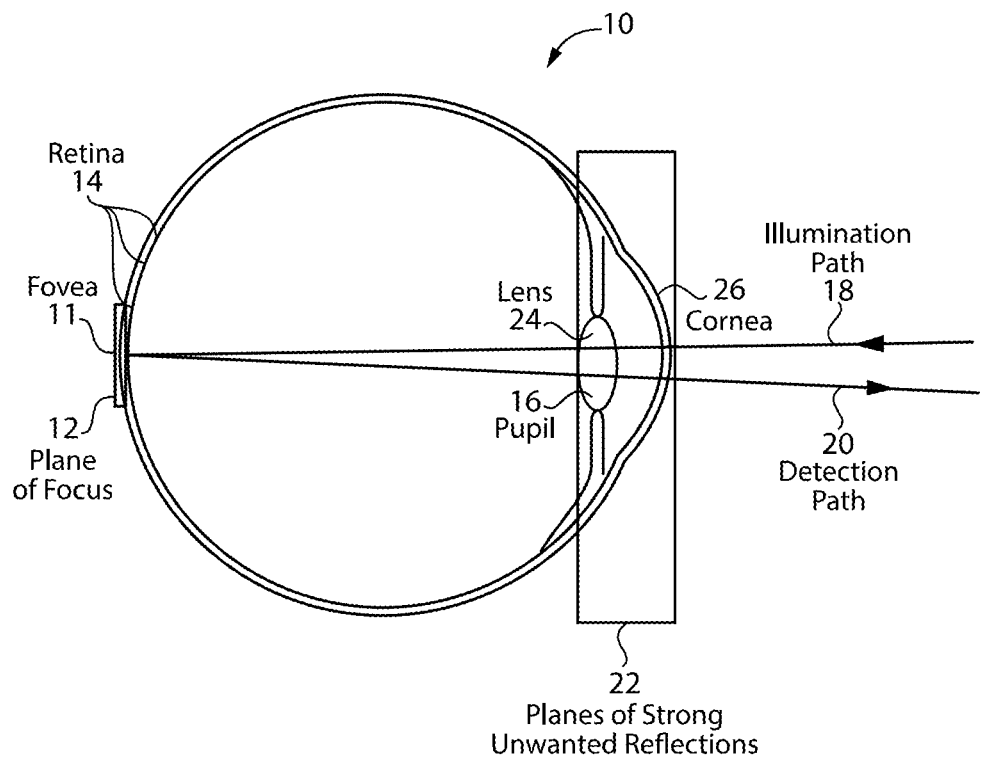
FIG. 1 is a schematic diagram of an eye showing selected tissues with the pupil through which light from the visual display is projected.

FIG. 1 illustrates a schematic diagram of an eye 10 showing selected tissues including a pupil 16 through which light from a light source provides a visual stimuli, such as a visual display, is projected, a retinal plane 12 as the target plane of focus for the projection of visual stimuli and imaging of retinal and subretinal structures, a cornea 26, a lens 24, and other anterior segment structures. As used herein, "visual display" is used to describe a device that transmits a visible or non-visible light image directed toward and received by the eye of a patient. Once received by the eye, the patient undertakes tasks that determine one or more aspects of visual function, which includes but is not limited to visual acuity.

Depending on the condition of the various tissues of the eye, strong unwanted reflections and locations of potential unwanted light scatter, aberrations and lack of transmissivity due to pathological conditions or aging negatively impact the retinal images appear at an anterior segment 22 of the eye 10. The unwanted reflections negatively impact the retinal images and locations of potential unwanted light scatter aberrations and lack of transmissivity due to pathological conditions or aging. The anterior segment 22 is generally located at or near the pupil 16, the lens 24, and the cornea 26. Retinal diseases including, but not limited to, diabetic macular edema and exudative age-related macular degeneration can elevate one or more portions of the retina so that the plane of focus is moved closer to the plane of the pupil, and the habitual refraction is in error. This leads to a visual stimulus that was formerly in focus on the retina but which is now being blurred. Such lack of retinal focus can occur to different extents at different retinal locations. The effects of this defocus can be corrected optically unless the retina is also damaged. The optical effects must be distinguished from the neural ones, so that potential visual function can be accurately specified.

To distinguish the optical effects from the neural effects, a device and system as described herein for measurement of potential visual function is particularly suited for guiding management of retinal disease and evaluating treatments for retinal disease in clinical trials. The described device and system identify the major factors that impact the retina 14 (see FIG. 1), that impact measurements of visual function, and that impact the potential vision that can be obtained with treatment. The device and systems include a noncontact system and do not require drops to dilate the pupil of the eye.

Referring to FIG. 1, virtually all the predetermined amount of light from a visual stimulus is projected though the pupil of the eye 16, along the illumination path 18. The plane of focus 12 of the visual stimulus is the retina 14, and specifically the layer within the retina for which the visual acuity is maximized. One of the main locations of interest to test retinal function is the fovea 11, which in a normal eye provides the best visual acuity and color vision, and is an important tissue in management decisions and clinical trial outcomes. To reach the retina, light must be focused by the cornea 26 and lens 24, either of which may have lost transparency or have degraded optics due to aging, disease, trauma, or adverse events related to treatment.

There are several conditions that negatively impact the illumination path 18, such as reduced pupil size decreasing the amount of light reaching the retina, which occurs naturally with aging. Pupil size is also reduced as a result of other condition such as drugs that constrict the pupil or neurological conditions. A pupil size that is larger than about 3 mm also negatively impacts the focus of both the Illumination path 18 and Detection path 20, due to focus varying across the pupil plane.

Further, light can fail to pass fully through the cornea 26, the lens 24, or any part of the anterior segment 22, depending on their condition. The anterior segment, for instance, can include numerous locations or areas that contain tissue alterations or aberrations, which can change the normal eye function and which can provide unwanted light scatter, or other aberrations and lack of transmissivity due to pathological conditions or due to aging. Both the amount of light reaching the retina and the accuracy of focus affect the measurements of visual function.

Information about the retina can be rendered inaccurately in the presence of small pupils that restrict light. The cornea 26, lens 24, or other location in the anterior segment 22 can have reduced transmissivity or fail to focus the light onto the retina 14. The structure of the retina 14 can be altered by disease or trauma so that it is elevated and which shortens the distance between the elevated structure making it too close to the cornea 26 to achieve an optimal focus at one or more locations. All of these factors also can reduce the quality of an image of the retina 14 that is captured along the detection path 20, when the light must exit through them on the way to an imaging device. The image of the retina 14, under different conditions, indicates the status of the retina 14, the locus of fixation, and the stability of fixation by comparing the retinal landmarks with the location of a visual stimulus that is projected through the pupil 16. The retinal image determines the relative location of a visual stimulus and the fovea 11 or other location on the retina 14.

Figure 2:
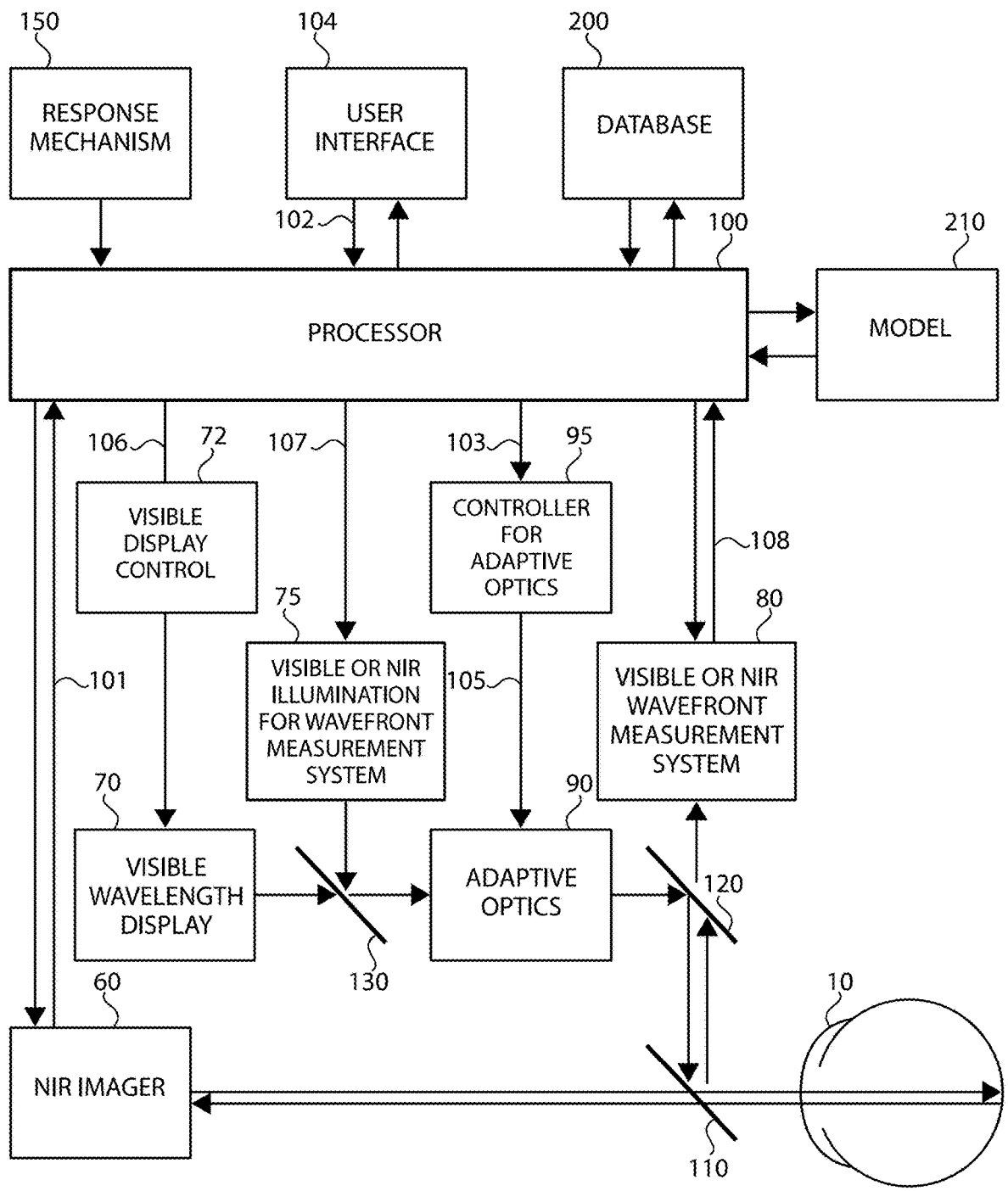
FIG. 2 is a schematic diagram of an optical imaging system used to measure visual function that includes a wavefront measurement subsystem to correct for aberrations of the eye.

FIG. 2 illustrates one embodiment of an optical imaging and visual display system 40 according to the present invention. A near infrared (NIR) imager 60 directs light to an eye 10 so that the light is directed toward the retina and is focused there to provide an accurate image. Those skilled in the art will recognize that a variety of different configurations can serve this function. In different embodiments, the NIR imager is a point scanning system or a line scanning system such as that in: Elsner et al., 1992; the Heidelberg Spectralis (Heidelberg Engineering, Heidelberg, Germany); U.S. Pat. Nos. 7,331,669, 7,831,106, or 8,237,835; and the Eidon Camera (iCare, Vantaa, Finland). In the preferred embodiment, the NIR illumination is sufficiently dim as to not interfere with judgements used in visual function measurements. U.S. Pat. Nos. 7,331,669, 7,831,106, and 8,237,835 are each incorporated by reference herein in their entirety.

Light returning from the retina to the NIR imager 60 is focused on the retina with sufficient accuracy to generate an image of the retina 14, which provides a clearly focused and excellent image for comparison with locations of targets projected with the visible wavelength display 70. The illumination and the detection properties of the NIR imager 60 provide both confocal and multiply scattered light imaging, as described in Elsner et. al. 2020 and also U.S. Pat. Nos. 7,331,669, 7,831,106, 8,237,835, and 8,488,895. The processor 100, which includes of one or more processors including, but not limited to computers, microcomputers, and electronic control devices. In different embodiments, the processor 100 includes memory for storage of the received data or includes a transmitter for the transmission of data. In other embodiments, the memory or transmitter are located externally to the processor 100. The processor 100 also controls the imager 60 through data collection and control lines 101 so that the properties of the NIR imager 60 enable the imaging of both light transmitted to the eye and properties of the sensor for the NIR imager 60. The parameters of the images or image data include, but are not limited to, intensity, gain, mode of imaging, polarization properties, wavelength, width of illumination on the retina, or field of view of a transmitted light wave, and are selectable by an operator. The operator adjusts the function of the imager 60 over control lines 102 through an input device, such as a user interface 104, coupled to the processor 100, with control lines 102. The selected parameters are stored or recorded in the processor 100, its internal memory, or a connected memory, and are used in making a determination of visual function. As used herein, the user interface means one or more devices that allows the operator or patient to interact with the system 40 or control it by using displays of visual images of current or stored images; stored data; visualizations of results or normative values; voice or audio commands; touchscreen commands; user selectable buttons; or other features used to select, display, or control test testing procedure or results based on current or stored information.

A visible wavelength display 70, also controlled by the processor 100 via control lines 106, transmits light output that is directed towards the retina 14 in such a manner as to direct a predetermined amount and type of light through the pupil 16 and into the eye 10. A visible display controller 72 is connected between the processor 100 and the visible wavelength display 70 to adjust the output of the visible wavelength display. In other embodiments, the visible display controller 72 is not included and the processor 100 is configured to adjust the functions of the visible display controller 72. The directed light, in one or more embodiments, is directed using Maxwellian view, also known as Kohler illumination, and thus in a manner so that the illumination on the retina 14, is identifiable and consistently reproducible, and is made constant from one eye to the next, either for a single patient or multiple patients. The display 70, in one embodiment, includes a one or two dimensional display including but not limited to a digital light projector, a liquid crystal display screen, liquid crystal on silicon, a cathodoluminescent display, an electroluminescent display, a photoluminescent display, a plasma display panel, an incandescent display, light emitting diodes, combinations thereof, or any similar optical display that projects a visual stimulus. In different embodiments, the visual stimulus is one or more of predetermined images that are stored in a memory, which is located internally or externally to the processor 100.

The processor 100 transmits the commands to project the visual stimuli, which are generated or stored in memory, through a control line 106 that controls the displayed images of the display 70, including but not limited to one or more patterns of visual stimuli, the intensity of the patterns, the timing of images being displayed, the movement of the images, the location of the display on the retina, and the color of the image. An output of an additional visible or NIR illumination for the wavefront measurement system 75, also controlled by the processor 100, through control lines 107, is combined with the output of light from the visible wavelength display 70 by a beam shaper and combiner 130.

The processor 100 controls the parameters of this light source, i.e. the visible wavelength display 75, including but not limited to, the image, the pattern, the intensity, the timing, movement, the location on the retina, and the color. The combined light output of the visible wavelength display 70 and illumination for the wavefront measurement system 75 is directed to an adaptive optics component 90, including one or more optical elements that are adjustable. The adjustment of the adaptive optics 90 is controllable by a controller for the adaptive optics 95 by control lines 105 so that the focus of the illumination on the retina 14 is improved beyond that accomplished by correcting only the sphere and cylinder. The adaptive optics controller 95 is controlled by the processor 100 through control lines 103. This combined light output is directed off a beam combiner 120 and toward the eye where it is combined with the light from the NIR imager 60 at a beam combiner 110. The light from all three sources, that of the NIR imager 60, the visible wavelength display 70, and the illumination for the wavefront measurement system 75, are all directed through the pupil of the eye and focused on the retina, with the visible wavelength display 70 and illumination for the wavefront measurement system focused by the adaptive optics component 90. The NIR imager 60 is focused by internal components via control from the processor 100 that is in communication with both the NIR imager 60 and the wavefront measurement system 80. Light returning from the retina 14 passes through the pupil 16 of the eye 10. The amount of light projected through the pupil is computed from wavefront measurement data, the NIR image intensity, or other features of image data or measurement from the retina of the patient. In addition, the property of light returning from the eye and analyzed by the processor includes, but is not limited to, fluorescence, coherence, or polarization, either at each location or in aggregate over a wider area.

U.S. Pat. No. 7,416,305 to Williams et al. ("Williams et al.") is distinguished from the present invention in that Williams requires that the image of the retina must be a high resolution image which is improved by adaptive optics to provide a higher contrast image than the image received from the retina without adaptive optics. In the present disclosure, however, the image of the retina does not need to be a high resolution image nor is the received image improved by the adaptive optics. In Williams et al., the adaptive optics serve as a compensating optical device that is adjusted to provide a high resolution, high contrast image of the retina using calculated wave aberrations. In contrast, the adaptive optics 90 of the present disclosure are operated to improve the quality of the visual stimulus on the retina and do not alter the retinal imager NIR imager 60.

The need to use an objective optical correction for a visual function test that is obtained at and according to the location of fixation is demonstrated because a patient with retinal damage in the fovea often uses a fixation location that is peripheral to the fovea. Further, the visual stimuli are distant from the fovea when peripheral vision is tested. Although the fovea is typically where fixation would have been located in a normal eye during the performance of a visual function test, the location of the fixation in a patient with retinal damage is often distant from the fovea. The optical errors corresponding to this location are unlikely to have been documented in previous eye examinations or refractions. It is difficult to measure these off-axis optical errors by subjective refraction. Yet, it has been demonstrated in the prior art that improving the focus by use of adaptive optics improves performance for a visual function test, for both on axis viewing, i.e. using the fovea to fixate the visual stimulus and off axis viewing, i.e. eccentric viewing, Rossi et al., 2007 and Lewis, P., Baskaran, K., Rosén, R., Lundström, L., Unsbo, P., & Gustafsson, J. (2014). Objectively determined refraction improves peripheral vision. *Optometry and vision science: official publication of the American Academy of Optometry*, 91(7), 740-746. respectively. In particular, Lewis and colleagues teach that it is important to use an objectively determined refraction for visual function at peripheral locations. However, the wavefront aberrations at these eccentric locations cannot be measured by means of retinal imaging instrumentation that has a small field of view unless the instrument can be pointed at the specific location and held at an accurate position during the optical measurements. Unless wider field, video rate retinal imaging is used, this positioning and accurate optical measurements are difficult due to eye movements by the patient. The requirement of measurements over a wide range of potential locations and accurate positioning is one distinction from U.S. Pat. No. 7,416,305 Williams, which describes a single retinal imaging device with high resolution high resolution and has only one wavefront measurement system. This system does not provide detailed wavefront measurements over a wide enough retinal area with accurate positioning to support use for eccentric viewing. In the extreme of high resolution, diffraction limited imaging is possible for the human retina for a field of view that is limited to approximately 2 deg at most for an eye with normal optics. The previous methods described by Burns et al., 2019 and colleagues and by Williams do not have a sufficiently wide field retinal imaging system to use adaptive optics for high resolution images across eccentric fixation locations or for testing peripheral visual stimuli.

The present disclosure, therefore, does not rely on a single feature resulting from imaging of the eye, but instead uses a combination of perceived features, including but not limited to, retinal imaging features with a wide field of view to determining fixation location and stability combined with wavefront measurements. A high resolution image, which has been compensated for wave aberrations, like that of Williams, does not provide the type of information used in the present disclosure. For instance, in Williams, the size of the retinal image for which the optical compensation can be achieved must be limited to an isoplanatic patch that is too small for an area to localize fixation when a patient has fixation instability or uses eccentric viewing, as stated above. A small retinal area also provides incomplete information about retinal landmarks or retinal status. Thus, the Williams method cannot be used because the field of view for a high resolution image generated by Williams is too small.

In addition the use of high resolution retinal images prevents the use of multiply scattered light to produce a retinal image, since the high spatial frequency information in the image is found predominantly in light that passes through the confocal aperture rather than being rejected. Further, in the present invention the improvement of the visual stimulus on the retina is embedded into a statistical framework, i.e statistical model, to determine the potential performance on a visual function test and the limits imposed by optical or other factors, whereas the Williams invention is directed to an implementation for use in refractive surgery or to fabricate a contact lens that improves vision in the real world beyond defocus and astigmatism. Finally, Williams specifies that the technique of wavefront measurement is limited to a point source for illumination, and which specifically uses the method of a Hartmann Shack sensor. The present method, in contrast, is not limited to the Hartmann Shack method, such as described in 1994 by Liang and colleagues: Liang J, Grimm B, Goelz S, Bille J F. Objective measurement of wave aberrations of the human eye with the use of a Hartmann-Shack wave-front sensor. J Opt Soc Am (A) 1994; 11:1949-57. Examples of other methods include laser ray tracing, the spatially resolved refractometer, compared with the Hartmann Shack method inMoreno-Barriuso E, Marcos S, Navarro R, Burns S A. Comparing laser ray tracing, the spatially resolved refractometer, and the Hartmann-Shack sensor to measure the ocular wave aberration. Optom Vis Sci. 2001 March; 78(3):152-6. doi: 10.1097/00006324-200103000-00007. PMID: 11327676 and the pyramidal wavefront sensing method, for instance as described in Singh N K, Jaskulski M, Ramasubramanian V, Meyer D, Reed O, Rickert M E, Bradley A, Kollbaum P S. Validation of a Clinical Aberrometer Using Pyramidal Wavefront Sensing. Optom Vis Sci. 2019 October; 96(10): 733-744. doi: 10.1097/OPX.0000000000001435. PMID: 31592956.

The present invention, while using a point source for illumination of a wavefront sensor, in one embodiment, also uses in other embodiments the visible wavelength display 70 or the retinal image to compute the wavefront compensation needed. In other embodiments, the Hartman Shack sensor or other methods such as the pyramidal wavefront sensing method to correct the focus of a visual display on the retina are used. The present invention also reports out the data from the wavefront correction for use in the statistical model to identify and to clarify the sources of degradation of visual performance which are used to compute the expected performance.

The NIR light returning from the eye 10 passes through the beam combiner 110 and is directed back to the NIR imager 60, where an image of the retina 14 is formed. A fundus image, including a retina image, is transmitted to the processor 100 through the data collection and control lines 101 for storage and analysis. Since the location of the coordinates of the projection of the visible wavelength stimulus on the retina is known, the NIR image provides the means to register the location of the visible wavelength stimulus on the retina to the known retinal landmarks. These include but are not limited to retinal blood vessels, the optic nerve head, peripapillary atrophy, the foveal light reflex, atrophy, hemorrhage, neovascular membranes, epiretinal membranes and gliosis, pigmentary changes, and polarization changes. This provides the locus of fixation, which is also known as the preferred retinal locus, and the variation of the locus of fixation, also known as fixation instability. The retinal image further provides information about the status of the retina at the location on the retina where the visible wavelength display is focused. The fixation information and retinal status information relative to the location of the visual stimuli on the retina is displayed as a graphics overlay, stored numerically by a computer as a numerical database, or both, by using the processor 100 and the user interface 104.

Light returning from the eye 10 that is not intended to be directed to the NIR imager 60 is directed off beam combiner 110 and towards beam combiner 120. The light that is of the wavelength range from the visible illumination or NIR illumination for the wavefront measurement system 75 is directed toward a visible or NIR wavefront measurement system 80 that provides data to the processor 100 through data collection and control lines 108 to quantify the optical aberrations of the light returning from the retina 14 as measured in the pupil plane 22. In other embodiments, data for images of different illumination wavelengths other than NIR or long wavelength visible illumination are directed to the processor. The wavefront measurement system 80 also communicates hardware and/or software related data to the processor 100 through data collection and control lines 108 to allow precise control of the wavefront measurement system 80 by the processor 100, including but not limited to timing, gain, number of samples to be included in each measurement, position of samples to be included in each measurement, whether controlled by measurement under the command of the processor or post processing that follows the acquisition of data that is sent to the processor. This wavefront measurement data is optimized by the processor 100 to provide sufficiently accurate information to focus the visual stimulus on the retina while being sufficiently dim or not simultaneously introducing visible illumination to interfere with the measurement of visual function.

A control loop for the adaptive optics 90 is formed by the wavefront measurement system 80, the processor 100, the controller for adaptive optics 95, and the adaptive optics 90, based on the measurement of the focus of the illumination for the wavefront measurement system 75 on the retina 14. The wavefront aberrations are computed, and those that can be corrected by the adaptive optics are identified as correctable, recorded, and saved as data in a database. Additionally, those that cannot be corrected or are impractical to correct and result in residual optical errors are also identified as not correctable, recorded, and saved as data.

Certain types of aberrations are not readily correctable, i.e. the very high order ones, and are not needed to make acceptable vision corrections. The present disclosure provides a cost effective solution, i.e. eliminate the large visual errors and quantifies the residual errors that are often not correctable at all or are not correctable at an acceptable price. Consequently, the present disclosure does not aim at the best ever focus that will not be or is not available in the real world with spectacles, and difficult to provide in contact lenses, or even an intraocular lens implant (IOL). Therefore, the present disclosure, in one or more embodiments, uses mirrors and an optical design to provide correction of lower order aberrations and some higher order wavefront errors. In some embodiments, adaptive optics are utilized that move sufficiently to tilt the imaging rays back to where they should be directed. The excessive cost of the fine tuning of many mirrors make correction of the very high order aberrations impractical, and some of these change rapidly over time with tear film.

A response mechanism 150 reports judgements about the visible wavelength stimulus by the patient, including but not limited to whether a target was seen, which direction a letter pointed, and the color, and provides input into the processor. In one embodiment, the response mechanism 150 is operated by the patient. In another embodiment, the response mechanism is a user interface 104 for the operator who inputs the patient's responses.

The decisions about whether a target is correctly seen are then used to control the next visible wavelength stimulus by the processor 100, for the measurement of visual function. This next visible wavelength stimulus, in one or more embodiments, is based on the patient's response or a predetermined sequence. A database 200 in communication with the processor 100 stores the current responses, the past responses, and any data relevant to determining the visual function. The processor 100 further processes the retinal images from the NIR imager 60 received over control lines 101 to specify the status of the retina 14 at the location of the target. Included in the status of the retina are the results from confocal and multiply scattered light imaging, indicating changes in signal amplitude that indicate irregular retinal or subretinal absorptions from blood or pigment defects, along with computations that indicate elevation or thickening of subretinal structures or motion of blood cells or other particles through the vessels. The database 200 includes results from the system that includes the retinal image, the location of the target on the retina, the stability of fixation, results from processing the retinal image or artificial intelligence from the retinal image data, the status of the retina, the status of the retina at the location of the target, the results from the visual function that was measured including both central tendency and variability, the wavefront errors prior to correction, and the wavefront errors that can be corrected versus those that cannot be corrected.

The database also includes other relevant clinical data and demographic data, including but not limited to, the retinal status from other instrumentation such as color fundus photographs, scanning laser ophthalmoscopy, vascular maps from scanning laser ophthalmoscopy, optical coherence tomography, optical coherence tomography angiography, or any of these used with adaptive optics, along with the wavefront aberration or optical measurements from other instrumentation, age, sex, diagnosis, treatment history, and results from other measurements of visual function.

A model 210 is in communication with the processor 100, and uses the data stored in the database 200 to provide a statistical estimate of the central tendency for a visual function and the variability, so that a range of potential vision that might be achieved is quantified. Central tendency is a single value that attempts to describe a set of data by identifying the central position within that set of data. This includes the unrelated optical factors such as small pupil, poor cornea or tear film optics, cataractous lens, incorrect plane of focus due to a poor refraction, and other factors for which some can be mitigated during measurements with the disclosed system to determine more accurately the status of the retina and the potential for improvement with treatment. In one embodiment, the metric of central tendency is the mean, and the variability metric is the variance, providing statistical limits for the significance of confounding reasons for reduced vision in the form of upper and lower confidence limits that can be set according to the probability of falling outside the confidence limits by a specific probability, e.g. 95% confidence limits. Further, reporting out of the wavefront errors shows how vision measurements are limited in a cataract.

The unique statistical analysis combines the information from the variety of sources described above to place bounds on the expected performance. For example, to address the visual acuity that a specific eye could potentially achieve with retinal treatment, bounds are determined such as from the confidence limits derived from the central tendency (expected value) and variability, including optical errors, fixation data, and other data. Using the aberrations that have been measured and found to be correctable, the upper and lower bounds on the visual acuity that is potentially achievable are determined. For instance with a Log MAR measurement, which is based on measurements of visual acuity, one method includes tumbling E's and 4 alternative forced choice. The statistical analysis includes the determination of whether optical and neural, as well as other factors, are independent or whether they must be modelled as interacting. A key tenet of the model includes the collection of data to determine whether the variables are independent and the overall variance is equal to the sum of the variance of individual factors. The system quantifies this status that includes the expectation for vision with successful retinal treatment or if elimination of unrelated factors such as lens opacities can be achieved.

Conversely, the model, in different embodiments, requires a function beyond simple addition of the variances of two or more variables that must be used to compute the expected visual function performance once the optical factors are corrected. Further, each of the variables may have a function more complex than a Gaussian distribution, and the variance may be distributed in a manner that is not symmetric around a mean value nor scaled linearly with the mean value. The combined variance is used to compute the upper and lower confidence limits. These confidence limits, i.e. the bounds used to interpret a visual function test score, become broader or narrower, depending on the values of and the function that combines the variances for the component factors. The upper bound corresponds by definition to the value that the visual function measurement must exceed for the retinal treatment to be considered a success, or to count as improvement in longitudinal measurements. The lower bound corresponds by definition to the value that the visual function must exceed or be considered as not worsening on follow-up. The lower bound is also the value that the visual function must exceed if treatment is considered effective when the goal is maintaining vision over time. These values may be related to current metrics, such as lines of vision gained or lost, that lack the important assessment of the influence of optical, fixation stability, or other factors.

The present invention has the following features: 1) Provides an assessment of fixation location using video rate and near infrared retinal imaging that is invisible to the patient; 2) provides an assessment of fixation stability using the same video rate near infrared retinal imaging; 3) Identifies the optical errors of a patient's eye not limited to sphere and cylinder, including those resulting from pathological conditions or aging conditions found in the cornea, lens, or pupil, collected by wavefront sensor measurement of the light returning from the retina; 4) provides an objective correction during the measurement of visual function of the main optical errors of a patient's eye, which is not limited to sphere and cylinder, using the wavefront measurements discussed above in item 3 above with adaptive optics; 5) projects a visual target onto the retina through a fixed size pupil of the instrument to reduce the enormous variability due to individual differences in pupil size; 6) provides an analysis of the retinal images with confocal and multiply scattered light, detailing the exact pathology at the point of fixation that is used by the patient in the vision test, clarifying the status of the retina at that location by use of confocal or multiply scattered light imaging and combinations of information from different imaging modes as described by U.S. Pat. Nos. 7,331,669, 7,831,106, 8,237,835, and 8,488,895; and 7) uses a novel system for measuring potential vision that includes a combination of all the components 1 through 6 described above, using a unique statistical analysis.

Figure 3:
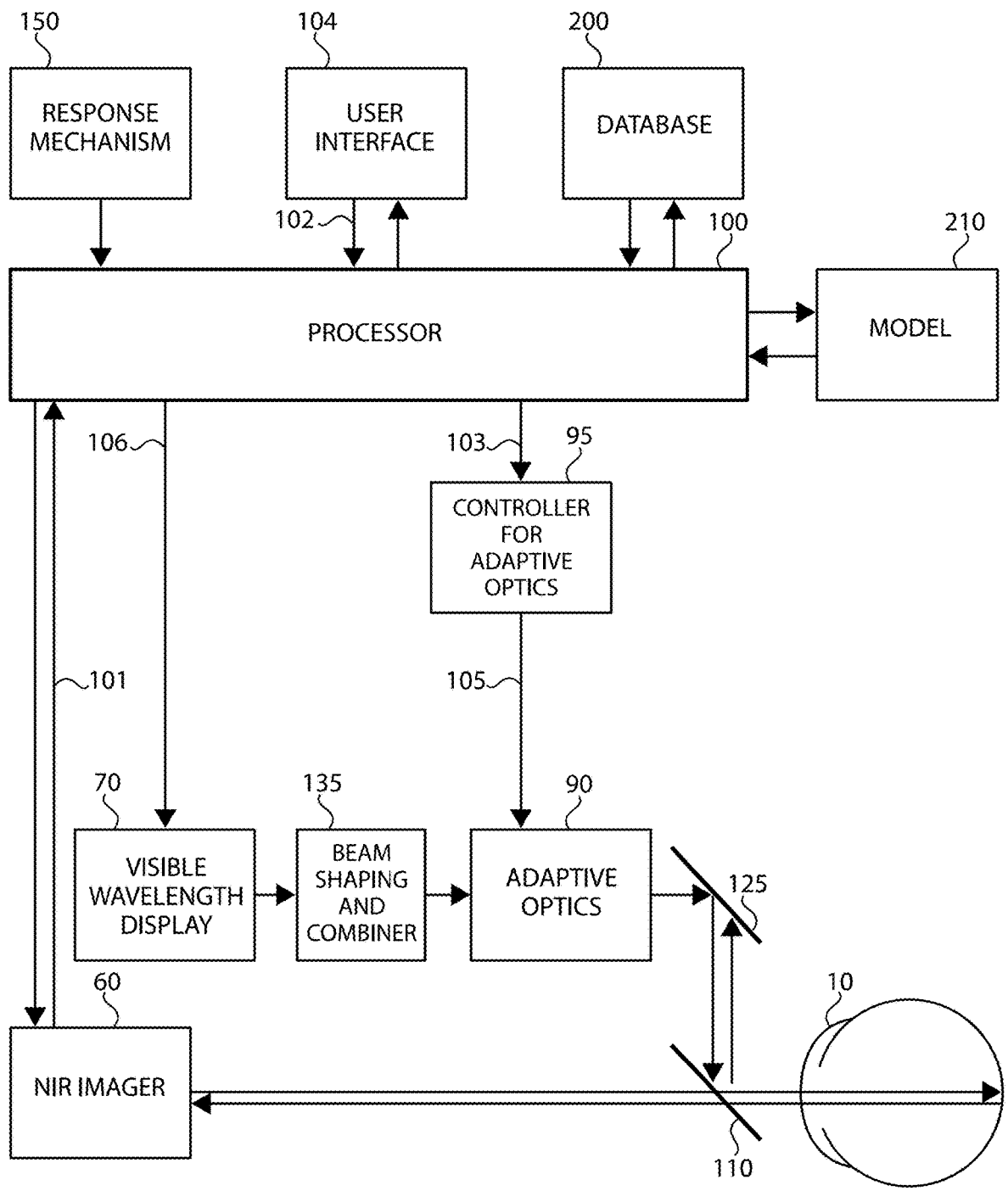
FIG. 3 is a schematic diagram of an optical imaging system used to measure visual function that does not include a wavefront measurement subsystem.

FIG. 3 illustrates another embodiment of an optical imaging and visual display system 50 according to the present invention. A near infrared (NIR) imager 60, i.e. imaging device, directs light to an eye 10 so that the light is directed toward the retina and is focused there to provide an accurate image. Those skilled in the art will recognize that a variety of different configurations serve this function. In different embodiments, the NIR imager is a point scanning system or a line scanning system such as that described in Elsner et al., 1992 and the Heidelberg Spectralis (Heidelberg Engineering, Heidelberg, Germany) and U.S. Pat. Nos. 7,331,669, 7,831,106, or 8,237,835 and the Eidon Camera (iCare, Vantaa, Finland). The imaging device 60 illuminates the retina by scanning the illumination across the retina or by projecting a series of illuminated regions onto the retina with light from the retina detected in synchrony. In one embodiment, the imaging device 60 has a wide field of view, i.e. from about 8 to 60 degrees visual angle, to allow for eccentric fixation and determination of retinal landmarks. Light returning from the retina to the NIR imager 60 is focused on the retina with sufficient accuracy to generate an image of the retina 14, which provides a clearly focused and excellent image for comparison with locations of targets projected with the Visible wavelength display 70. The illumination and the detection properties of the NIR imager 60 provide both confocal and multiply scattered light imaging, as described in Elsner et al., 2020. The images or data that are used to compute an image are directed to the processor 100, which consists of one or more processors including computers, microcomputers, and electronic control devices. In different embodiments, the processor 100 includes memory for storage of the received data or includes a transmitter for the transmission of data. In other embodiments, the memory or transmitter are located externally to the processor 100. The processor 100 also controls the imager 60 through data collection and control lines 101 so that the properties of the NIR imager 60 enable the imaging of both light transmitted to the eye and properties of the sensor for the NIR imager 60. The properties include but are not limited to intensity, gain, mode of imaging, polarization properties, wavelength, width of illumination on the retina, or field of view of a transmitted light wave, and are selectable by an operator. The operator adjusts the function of the imager 60 over control lines 102 through an input device, such as a user interface 104, coupled to the processor 100, with control lines 102. The selected parameters are stored or recorded in the processor 100 and used in making a determination of visual function.

A visible wavelength display 70, also controlled by the processor 100 via control lines 106, has light output that is directed towards the retina 14 in such a manner as to direct a known amount and type of light through the pupil 16 and into the eye 10. The directed light, in one or more embodiments, is directed using Maxwellian view, also known as Kohler illumination, and thus in a manner so that the illumination on the retina 14 is identifiable and consistently reproducible, and is made constant from one eye to the next, either for a single patient or multiple patients. The display 70, in one embodiment, includes a one or two dimensional display including but not limited to a digital light projector, a liquid crystal display screen, liquid crystal on silicon, a cathodoluminescent display, an electroluminescent display, a photoluminescent display, a plasma display panel, an incandescent display, light emitting diodes, combinations thereof, or any similar optical display that projects a visual stimulus. In different embodiments, the visual stimulus is one or more of predetermined images that are stored in a memory, which is located internally or externally to the processor 100. As used herein, the one dimensional display transmits a single line that is scanned across the retina.

The processor 100 transmits the commands to project the visual stimuli, which are generated or stored in memory, through a control line 106 that controls the displayed images of the display 70, including but not limited to the pattern of the visual stimuli, the intensity of the patterns, the timing of images being displayed, the movement of the images, the location of the display on the retina, and the color of the image. An output of the visible wavelength display 70 transmits light via a beam shaping and combiner component 135 to an adaptive optics component 90 to correct for wavefront errors by one or more optical elements that are adjustable. The adaptive optics component 90 is controlled by the controller for adaptive optics 95 through control lines 105. The controller for the adaptive optics 95 is controlled by the processor 100 through control lines 103.

The adjustment of the adaptive optics 90 is controllable by a controller for the adaptive optics 95 through control lines 105 so that the focus of the illumination on the retina 14 is improved beyond that accomplished by correcting only the sphere and cylinder. This combined light output is directed off a mirror, beam splitter, or filter 125 and toward the eye where it is combined with the light from the NIR imager 60 at a beam combiner 110. The light from both, that of the NIR imager 60 and the visible wavelength display 70, is directed through the pupil of the eye and focused on the retina, with the visible wavelength display 70 focused by the adaptive optics component 90. The NIR imager 60 is focused by internal components via control from the processor 100 that is in communication with the NIR imager 60. Light returning from the retina 14 passes through the pupil 16 of the eye 10.

The NIR light returning from the eye 10 passes through the beam combiner 110 and directed back to the NIR imager 60, where an image of the retina 14 is formed. The fundus image, including the retina image, is transmitted to the processor 100 through the data collection and control lines 101 for storage and analysis. Since the location of the coordinates of the projection of the visible wavelength stimulus on the retina is known, the NIR image provides the means to register the location of the visible wavelength stimulus on the retina to the known retinal landmarks, as noted above. This provides the locus of fixation, which is also known as the preferred retinal locus, and the variation of the locus of fixation, also known as fixation instability. The retinal image further provides information about the status of the retina at the location on the retina where the visible wavelength display is focused. The fixation information and retinal status information relative to the location of the visual stimuli on the retina is displayed as a graphics overlay, computer and stored numerically, or both, using the processor 100 and the user interface 104.

Light returning from the eye 10, that is not intended to be directed to the NIR imager 60, is directed off beam combiner 110 and towards mirror, beam splitter, or filter 125. The NIR imager 60 also provides data to the processor 100 through data collection and control lines 101 to quantify the optical aberrations of the light returning from the retina 14. This is known as sensorless adaptive optics, although there is illumination and a sensor included in the NIR imager 60, because there is not an additional illumination source and sensor (Burns et al., 2019) In one embodiment, the location of the target on the retina is used to limit the optical correction data to samples at that location, which is more precise than averaging over a portion of the retina that includes areas outside where the visual stimuli are projected, because, for instance, these may differ in retinal elevation, using the processor 100. As the present invention is not limited to a small field of view of the retina, which as a limitation inherent in Williams et al., the area of retina sampled can be optimized to provide an accurate focus for a specific location on the retina.

In the present invention, pathological features of the retina can be identified, which is important because such pathological features can alter the preferred plane of focus on the retina 14 for the visual function test at one retinal location more than at another retinal location. In another embodiment, the wavefront error is precomputed either from another device or measurements of the visual acuity that a specific eye could potentially achieve, and the position of the target on the retina, determined by the NIR imager, is used to specify the correction for wavefront error by the processor 100, and then transmitted to the controller for adaptive optics 95 via control lines 103. In one embodiment, signal enhancement for the wavefront error computation is produced by using structured illumination, as described in Clark et al., 2010, 2011; Elsner et al., 2011. This is accomplished whether the NIR imager is a point scanning system or a line scanning system such as that in Elsner et al., 1992; the Heidelberg Spectralis (Heidelberg Engineering, Heidelberg, Germany); U.S. Pat. Nos. 7,331,669, 7,831,106, or 8,237,835; and the Eidon Camera (iCare, Vantaa, Finland). The latter allows low cost and rapid alternations of illumination lines that are turned on vs. off, which provides a square wave grating for ease of Fourier or other analysis of optical transfer through the eye for sampling from a region of interest on the retina. The amount of light return from the retina of the NIR Imager 60 depends on pupil size, since there is little effect of fundus pigmentation, thereby reporting on a patient's pupil diameter in the absence of the wavefront measurement systems in FIGS. 2, 4, and 5, as described in Elsner et al., 2013.

A control loop for the adaptive optics 90 is formed by the NIR Imager 60 or data in the database 200, the processor 100, the controller for adaptive optics 95, and the adaptive optics 90, based on the measurements of the focus from the NIR imager 60 on the retina 14. The wavefront aberrations are computed, and those that can be corrected by the adaptive optics are reported, and also those that cannot be corrected or are impractical to correct and result in residual optical errors. In one embodiment, NIR imager 60 illumination is modulated temporally, and then frequency-based detection schemes in the detection mechanisms of the NIR imager 60 are used to achieve improved signal to noise ratio. Alternatives include simple flickering of the illumination as well as more complex schemes of homodyne and heterodyne detection by NIR imager 60, based on frequency. In one embodiment, NIR illumination for wavefront measurement is alternated temporally with the pattern of NIR illumination used to produce a more optimal retinal image for determination of retinal location of the visual target, fixation instability, or retinal status. In the preferred embodiment, the NIR illumination is sufficiently dim as to not interfere with judgements made by the patient and which are used in visual function measurements. In the preferred embodiment, the data from the focus and wavefront error computations are reported out in a manner that describes the lower order and higher order aberrations and estimated error in retinal focus due to wavefront errors. A response mechanism 150 reports judgements made by the patient regarding the visible wavelength stimulus perceived by the patient, including but not limited to whether a target was seen, which direction a letter pointed, and the color, and provides input into the processor. In one embodiment, the response mechanism is operated by the patient. In another embodiment, the response mechanism is a user interface 104 for the operator who inputs the patient's responses.

The decisions about whether a target is correctly seen, i.e., correctly identified, are then used to control the next visible wavelength stimulus by the processor 100, for the measurement of visual function. A database 200 in communication with the processor 100 stores the current responses, the past responses, and any data relevant to determining the visual function. The processor 100 further processes the retinal images from the NIR imager 60 received over control lines 101 to specify the status of the retina 14 at the location of the target. Included in the status of the retina are the results from confocal and multiply scattered light imaging, indicating changes in signal amplitude the indicate irregular retinal or subretinal absorptions from blood or pigment defects, along with computations that indicate elevation or thickening of subretinal structures or motion of blood cells or other particles through the vessels. The database 200 includes results from the system that includes the retinal image, the location of the target on the retina, the stability of fixation, results from processing the retinal image or artificial intelligence from the retinal image data, the status of the retina, the status of the retina at the location of the target, the results from the visual function that was measured including both central tendency and variability, the wavefront errors prior to correction, and the wavefront errors that can be corrected versus those that cannot be corrected.

The database 200 also includes other relevant clinical data and demographic data, including but not limited to the retinal status from other instrumentation such as color fundus photographs, scanning laser ophthalmoscopy, optical coherence tomography, optical coherence tomography angiography, or any of these used with adaptive optics, along with the wavefront aberration or optical measurements from other instrumentation, age, sex, diagnosis, treatment history, and results from other measurements of visual function. These data can be used to improve the computation of wavefront errors.

A model 210 is in communication with the processor 100, and uses the data stored in the database to provide a statistical estimate of the central tendency for a visual function and the variability, so that a range of potential vision that might be achieved is quantified as above. Central tendency is a single value that attempts to describe a set of data by identifying the central position within that set of data. This includes the unrelated optical factors such as small pupil, poor cornea or tear film optics, cataractous lens, incorrect plane of focus due to a poor refraction, and other factors for which some can be mitigated during measurements with the disclosed system to determine more accurately the status of the retina and the potential for improvement with treatment. The upper and lower bounds of performance on a visual task are computed and used as in the embodiments in FIG. 2.

Figure 4:
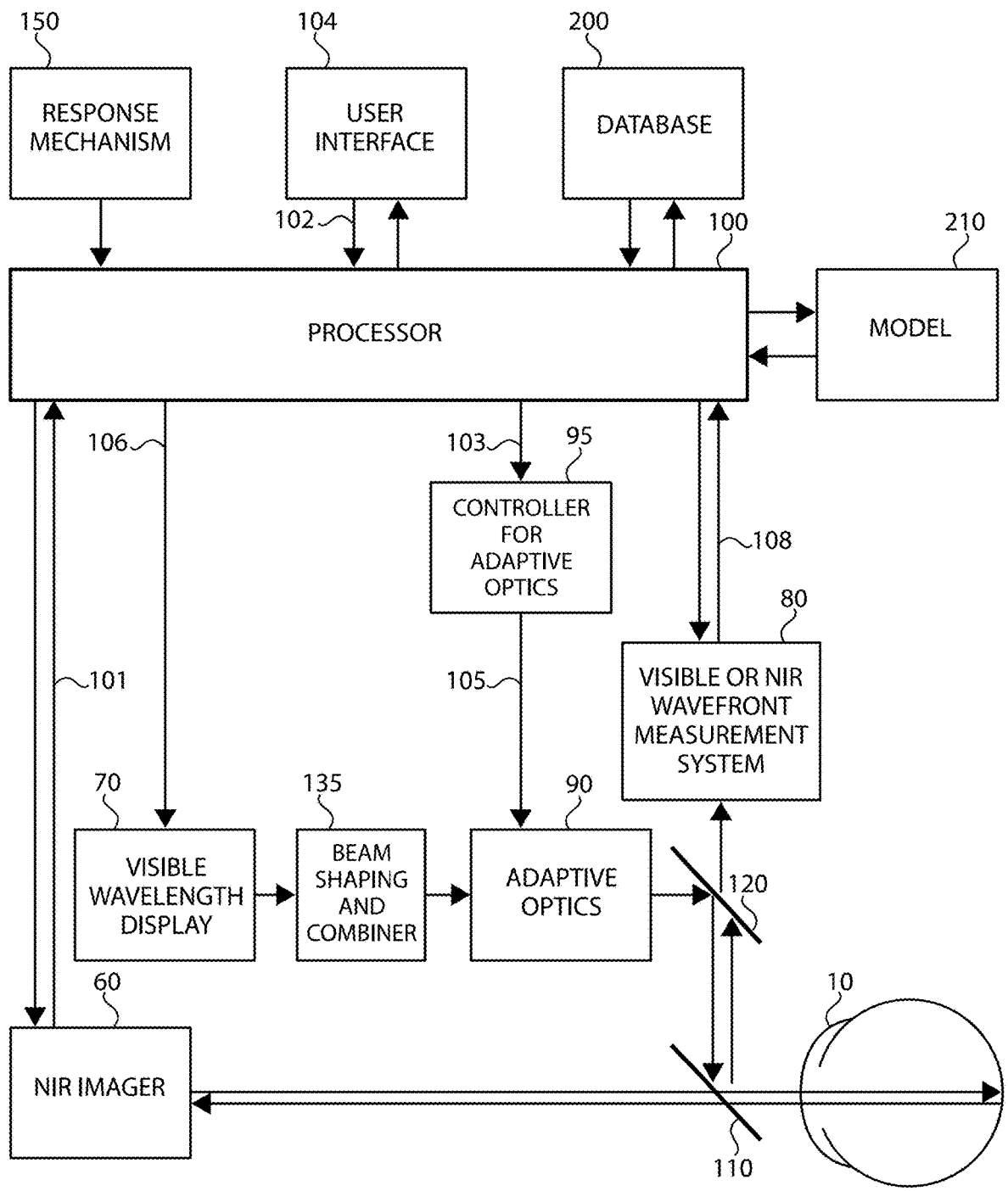
FIG. 4 is a schematic diagram of an optical imaging system used to measure visual function that includes a wavefront measurement subsystem that uses the visible wavelength display is the illumination source.

FIG. 4 illustrates another embodiment of an optical imaging and visual display system 40, according to the present invention. A NIR imager 60 with several embodiments as described above directs light to an eye 10 so that the light is directed toward the retina and is focused there to provide an accurate image. The functions are similar to that in FIGS. 2 and 3 except for certain changes that are described.

Light returning from the retina to the NIR imager 60 is focused on the retina with sufficient accuracy to generate an image of the retina 14, which provides a clearly focused and excellent image for comparison with locations of targets projected with the Visible wavelength display 70. The illumination and the detection properties of the NIR imager 60 provide both confocal and multiply scattered light imaging, as described in Elsner et al., 2020 and other descriptions in FIG. 2. The images or data that are used to compute an image are directed to the processor 100, which consists of one or more processors including computers, microcomputers, and electronic control devices. In different embodiments, the processor 100 includes memory for storage of the received data or includes a transmitter for the transmission of data. In other embodiments, the memory or transmitter are located externally to the processor 100. The processor 100 also controls the imager 60 through data collection and control lines 101 so that the properties of the NIR imager 60 enable the imaging of both light transmitted to the eye and properties of the sensor for the NIR imager 60. The properties include but are not limited to intensity, gain, mode of imaging, polarization properties, wavelength, width of illumination on the retina, or field of view of a transmitted light wave, and are selectable by an operator. The operator adjusts the function of the imager 60 over control lines 102 through an input device, such as a user interface 104, coupled to the processor 100, with control lines 102. The selected parameters are stored or recorded in the processor 100 and used in making a determination of visual function.

A visible wavelength display 70, also controlled by the processor 100 via control lines 106, has light output that is directed towards the retina 14 in such a manner as to direct a known amount and type of light through the pupil 16 and into the eye 10. The directed light, in one or more embodiments, is directed using Maxwellian view, also known as Kohler illumination, and thus in a manner so that the illumination on the retina 14, is identifiable and consistently reproducible, and is made constant from one eye to the next, either for a single patient or multiple patients. The display 70, in one embodiment, includes a one or two dimensional display including but not limited to a digital light projector, a liquid crystal display screen, liquid crystal on silicon, a cathodoluminescent display, an electroluminescent display, a photoluminescent display, a plasma display panel, an incandescent display, light emitting diodes, combinations thereof, or any similar optical display that projects a visual stimulus. In different embodiments, the visual stimulus is one or more of predetermined images that are stored in a memory, which is located internally or externally to the processor 100.

The processor 100 transmits the commands to project the visual stimuli, which are generated or stored in memory, through a control line 106 that controls the displayed images of the display 70, including but not limited to the pattern of the visual stimuli, the intensity of the patterns, the timing of images being displayed, the movement of the images, the location of the display on the retina, and the color of the image.

The light output of the visible wavelength display 70 is directed by beam shaping and combiner 135 to an adaptive optics component 90, including one or more optical elements that are adjustable. The adjustment of the adaptive optics 90 is controllable by a controller for the adaptive optics 95 by control lines 105 so that the focus of the illumination on the retina 14 is improved beyond that accomplished by correcting only the sphere and cylinder. The controller for the adaptive optics 95 is controlled by the processor 100 through control lines 103. This light output is directed off a beam combiner 120 and toward the eye where it is combined with the light from the NIR imager 60 at a beam combiner 110. The light from both sources, that of the NIR imager 60 and the visible wavelength display 70, are directed through the pupil of the eye and focused on the retina 14, with the visible wavelength display 70 by the adaptive optics component 90. The NIR imager 60 is focused by internal components via control from the processor 100 that is in communication with both the NIR imager 60 and the wavefront measurement system 80. Light returning from the retina 14 passes through the pupil 16 of the eye 10.

The NIR light returning from the eye 10 passes through the beam combiner 110 and is directed back to the NIR imager 60, where an image of the retina 14 is formed. The fundus image, including the retina image, is transmitted to the processor 100 through the data collection and control lines 101 for storage and analysis. Since the location of the coordinates of the projection of the visible wavelength stimulus on the retina is known, the NIR image provides the means to register the location of the visible wavelength stimulus on the retina to the known retinal landmarks. These include but are not limited to retinal blood vessels, the optic nerve head, peripapillary atrophy, the foveal light reflex, atrophy, hemorrhage, neovascular membranes, epiretinal membranes and gliosis, pigmentary changes, and polarization changes. This provides the locus of fixation, which is also known as the preferred retinal locus, and the variation of the locus of fixation, also known as fixation instability. The retinal image further provides information about the status of the retina at the location on the retina where the visible wavelength display is focused. The fixation information and retinal status information relative to the location of the visual stimuli on the retina is displayed as a graphics overlay, computer and stored numerically, or both, using the processor 100 and the user interface 104. Light returning from the eye 10 that is not intended to be directed to the NIR imager 60 is directed off beam combiner 110 and towards beam combiner 120. The light that is of the wavelength range from the visible wavelength display 70 is directed toward a visible or NIR wavefront measurement system 80 that provides data to the processor 100 through data collection and control lines 108 to quantify the optical aberrations of the light returning from the retina 14 as measured in the pupil plane 22. The wavefront measurement system 80 also communicates hardware and/or software related data to the processor 100 through data collection and control lines 108 to allow precise control of the wavefront measurement system 80 by the processor 100, including but not limited to timing, gain, number of samples to be included in each measurement, position of samples to be included in each measurement, whether controlled by measurement under the command of the processor or post processing that follows the acquisition of data that is sent to the processor.

A control loop for the adaptive optics 90 is formed by the wavefront measurement system 80, the processor 100, the controller for adaptive optics 95, and the adaptive optics 90, based on the measurement of the focus of the illumination from the visible wavelength display 70 on the retina 14. The wavefront aberrations are computed, and those that can be corrected by the adaptive optics are reported, and also those that cannot be corrected or are impractical to correct and result in residual optical errors. In one embodiment, illumination from the visible wavelength display 70 is modulated temporally, and then frequency-based detection schemes in the detection mechanisms the visible or NIR wavefront measurement system 80 are used to achieve improved signal to noise ratio. Alternatives include simple flickering of the illumination as well as more complex schemes of homodyne and heterodyne detection by visible or NIR wavefront measurement system 80, based on frequency. In one embodiment, the illumination for wavefront measurement is alternated temporally with the pattern used to test visual function. In the preferred embodiment, the NIR illumination of the NIR imager 60 is sufficiently dim as to not interfere with judgements used in visual function measurements. Similarly, in one preferred embodiment, the NIR illumination of the NIR imager 60 does not overlap the wavelength range of the visible wavelength display 70, so as to interfere with neither the wavefront measurements nor the visual function measurements. In the preferred embodiment, the data from the focus and wavefront error computations are reported out in a manner that describes the lower order and higher order aberrations and estimated error in retinal focus due to wavefront errors.

A response mechanism 150 reports judgements about the visible wavelength stimulus by the patient, including but not limited to whether a target was seen, which direction a letter pointed, and the color, and provides input into the processor. In one embodiment, the response mechanism 150 is operated by the patient. In another embodiment, the response mechanism is a user interface 104 for the operator who inputs the patient's responses.

The decisions about whether a target is correctly seen are then used to control the next visible wavelength stimulus by the processor 100, for the measurement of visual function. This next visible wavelength stimulus can be based on the patient's response or a predetermined sequence of visual targets. A database 200 in communication with the processor 100 stores the current responses, the past responses, and any data relevant to determining the visual function. The processor 100 further processes the retinal images from the NIR imager 60 received over control lines 101 to specify the status of the retina 14 at the location of the target. Included in the status of the retina are the results from confocal and multiply scattered light imaging, indicating changes in signal amplitude the indicate irregular retinal or subretinal absorptions from blood or pigment defects, along with computations that indicate elevation or thickening of subretinal structures or motion of blood cells or other particles through the vessels. The database 200 includes results from the system that includes the retinal image, the location of the target on the retina, the stability of fixation, results from processing the retinal image or artificial intelligence from the retinal image data, the status of the retina, the status of the retina at the location of the target, the results from the visual function that was measured including both central tendency and variability, the wavefront errors prior to correction, and the wavefront errors that can be corrected versus those that cannot be corrected.

The database also includes other relevant clinical data and demographic data, including but not limited to the retinal status from other instrumentation such as color fundus photographs, scanning laser ophthalmoscopy, optical coherence tomography, optical coherence tomography angiography, or any of these used with adaptive optics, along with the wavefront aberration or optical measurements from other instrumentation, age, sex, diagnosis, treatment history, and results from other measurements of visual function A model 210 is in communication with the processor 100, and uses the data stored in the database to provide a statistical estimate of the central tendency for a visual function and the variability, so that a range of potential vision that might be achieved is quantified, as above. Central tendency is a single value that attempts to describe a set of data by identifying the central position within that set of data. This includes the unrelated optical factors such as small pupil, poor cornea or tear film optics, cataractous lens, incorrect plane of focus due to a poor refraction, and other factors for which some can be mitigated during measurements with the disclosed system to determine more accurately the status of the retina and the potential for improvement with treatment. In one embodiment, the metric of central tendency is the mean, and the variability is the variance, providing statistical limits for the significance of confounding reasons for reduced vision in the form of upper and low confidence limits that can be set according to the probability of falling outside the confidence limits by a specific probability, e.g. 95% confidence limits. Further, reporting out of the wavefront errors shows how vision measurements are limited in a cataract. The upper and lower bounds of performance on a visual task are computed and used as in the embodiments in FIG. 2.

Figure 5:
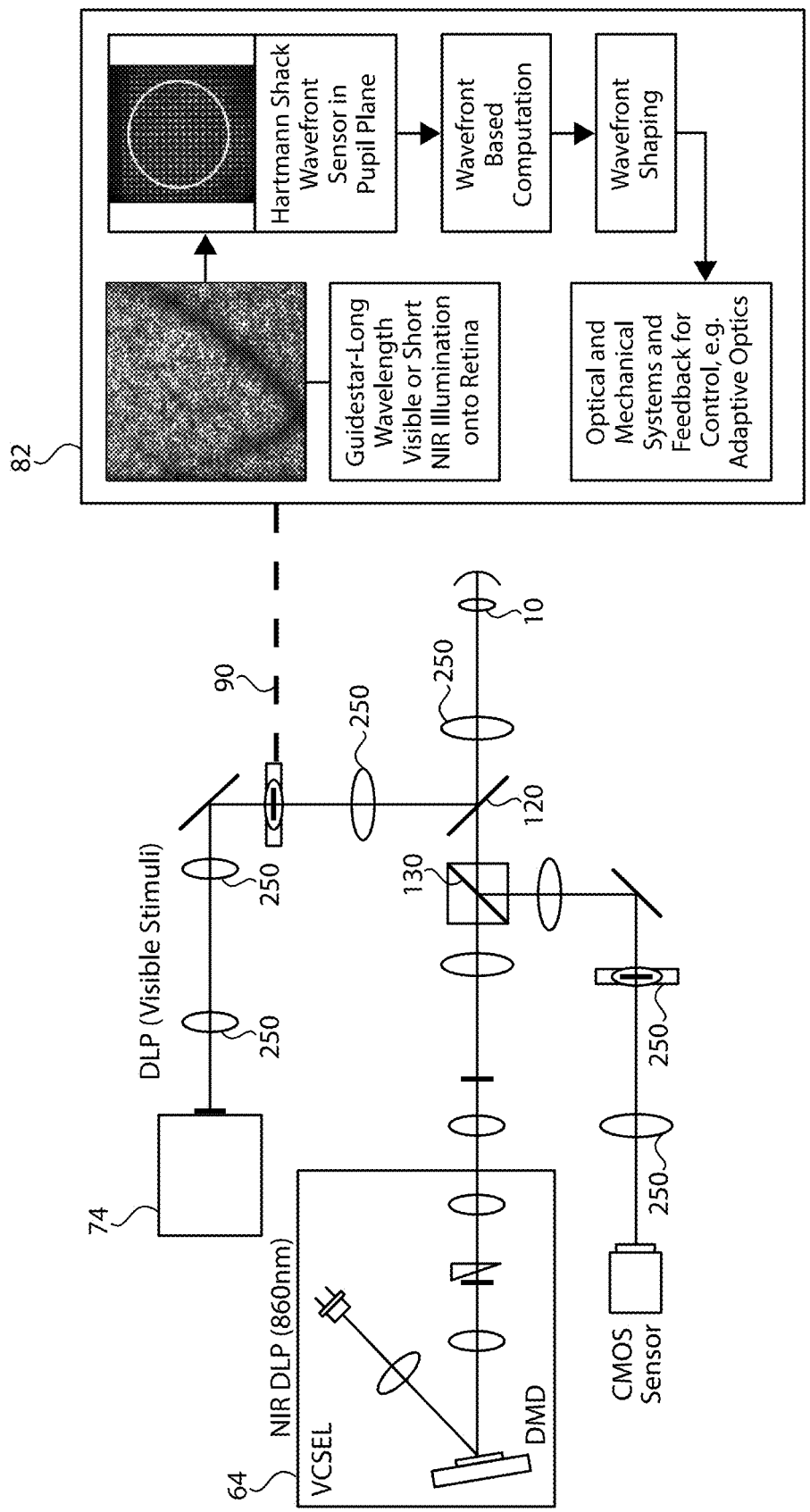
FIG. 5 is a schematic diagram of an illustrative embodiment of a device to determine visual function, in this case using the Hartmann Shack method of measurement of optical aberrations.

FIG. 5 illustrates another embodiment of an optical imaging and visual display system 40 to determine visual function while performing measurement of optical aberrations, with wavefront measurements using a Hartman-Shack sensor. The NIR or visible wavelength imager 64 is shown as a digital light projector (DLP) with digital mirrors (DMD) and an illumination source that is a vertical cavity surface emitting laser (VCSEL) as found in Muller M S, Elsner A E. Confocal Retinal Imaging Using a Digital Light Projector with a Near Infrared VCSEL Source. Proc SPIE Int Soc Opt Eng. 2018 February; 10546:105460G. doi: 10.1117/12.2290286. PMID: 29899586; PMCID: PMC5995569. The visible wavelength display 74, which uses another DLP as for illumination and pattern generation in this embodiment, is directed by additional focusing lenses 250 towards adaptive optics 90 under the control of a visible or NIR wavefront measurement system 82 for correction of wavefront aberrations to achieve a precise focus on the retina 14. The illumination from the NIR or Visible wavelength imager 64 is combined using a series of lenses 250 and a beam combiner 120 with the illumination from the visible wavelength display 74. The well-known Hartmann Shack method is implemented by using a visible or NIR wavefront measurement system 82 that evaluates the intensity and position of an array of points focused in the pupil plane that is produced by sampling light returning from the retina that is passed through a lenslet array, as described in Burns et al., 2019.

Figure 6A:
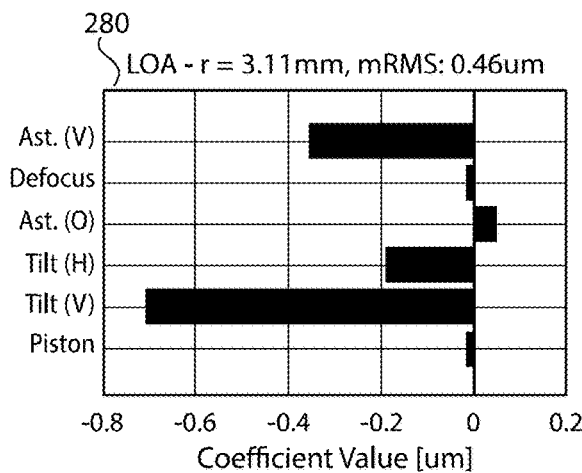
FIGS. 6A-D illustrate a sample graphical representation of lower and higher order aberrations (LOA) from near infrared (NIR) wavelength measurements, showing the effect of aging and of refractive error.
Figure 6B:
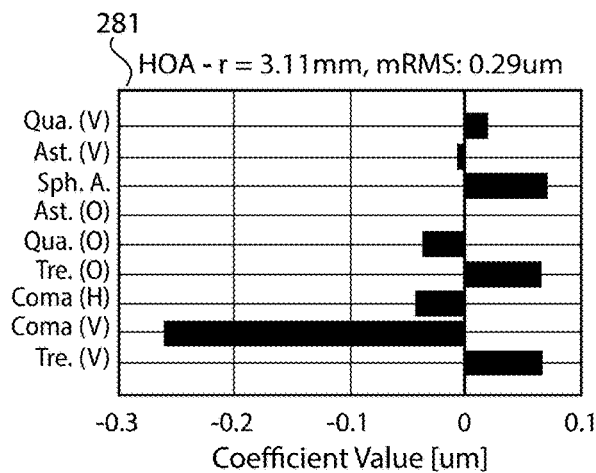
Figure 6C:
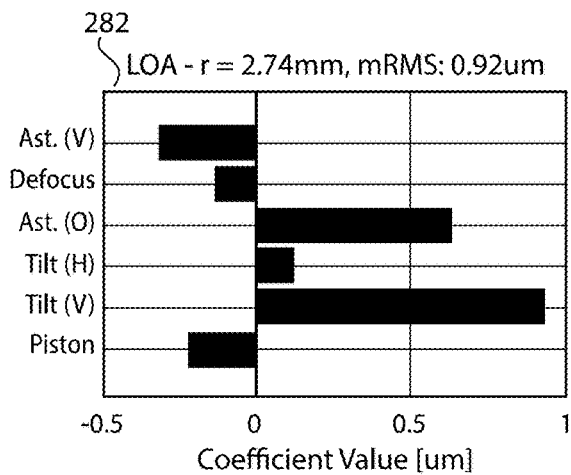
Figure 6D:
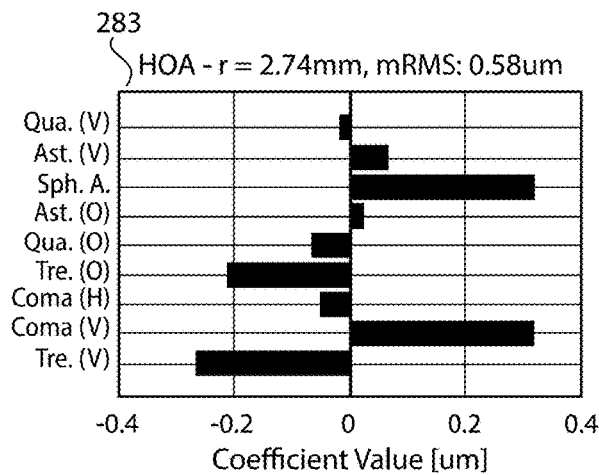

FIGS. 6A, 6B, 6C, and 6D describe a sample graphical representation of lower order aberrations (LOA) and higher order aberrations (HOA) from NIR wavelength measurements, showing the effect of aging and of refractive error. This also demonstrates that the pyramidal wavefront sensing method can be used in the present invention; i.e. the method of measuring wavefront aberrations is not limited to the Hartmann Shack method. On the top left, FIG. 6A, are results from an eye of a 30 year old patient who is emmetropic but with some astigmatism, yet nevertheless is expected to have minimal lower order aberrations 280. On the top right, FIG. 6B, are results from an eye of a 30 year old patient who is emmetropic but with some astigmatism, but is expected to have few lens changes due to aging and therefore is expected to have minimal higher order aberrations 281. On the bottom left, FIG. 6C, are results from an eye of a 71 year old patient who is myopic and therefore expected to have large lower order aberrations 282. On the bottom right, FIG. 6D, are results from an eye of a 71 year old patient who is myopic but is also expected to have aging changes of lens and tearfilm and therefore expected to have larger higher order aberrations 283. The left plots show astigmatism (vertical), defocus, astigmatism (overall), tilt (horizontal), tilt (vertical), and piston. The right plots show quadrafoil (vertical), astigmatism (vertical), spherical aberration, astigmatism (overall), trefoil (overall), coma (horizontal), coma (vertical), and trefoil (vertical).

Figure 7A:
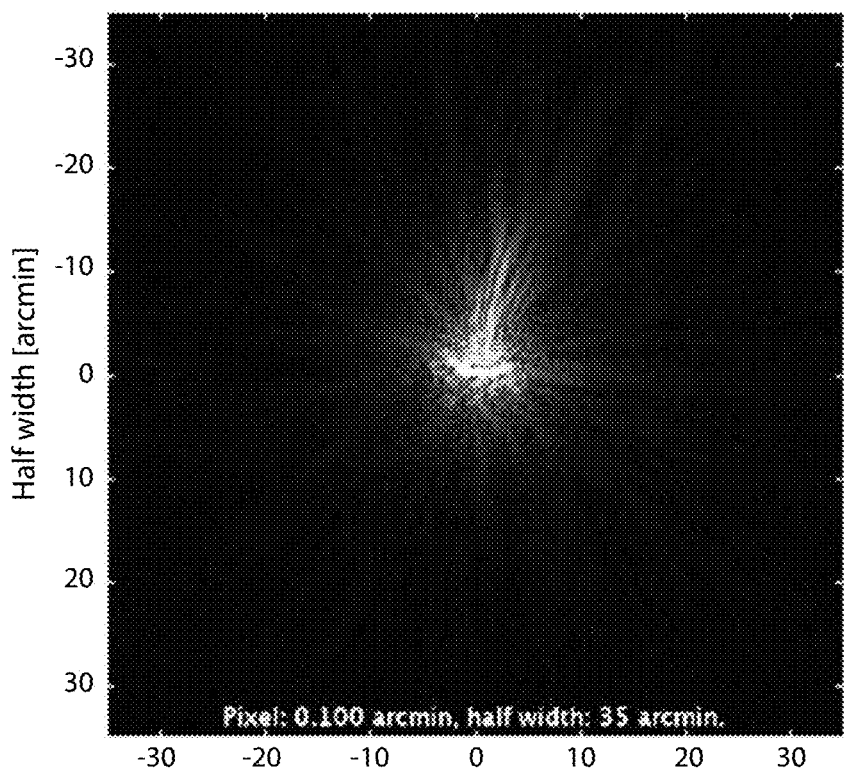
FIGS. 7A and 7B illustrate one method of documenting wavefront aberrations, illustrating the differences between the younger and older patients.
Figure 7B:
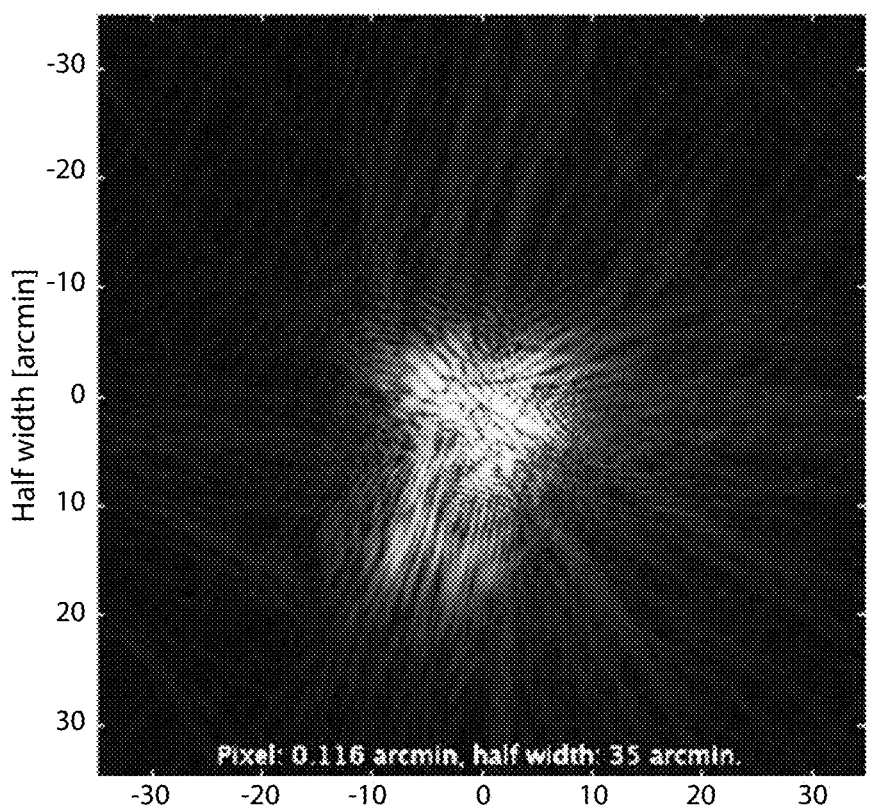

FIGS. 7A and 7B show another method of reporting out wavefront aberrations, illustrating the differences between the younger patient (FIG. 7A) and the older patient (FIG. 7B) for the computed deviation from a spot that is focused on the retina by the eye, known as the point spread function. The younger eye on the top has a distribution of light on the retina that is more compact, indicating better focus. The older eye on the bottom has a distribution that is not compact, and has a function more complex than mere defocus would produce. Again, this demonstrates that the pyramidal wavefront sensing method of the present invention; i.e. the method of measuring wavefront aberrations is not limited to the Hartmann Shack method.

Figure 8A:
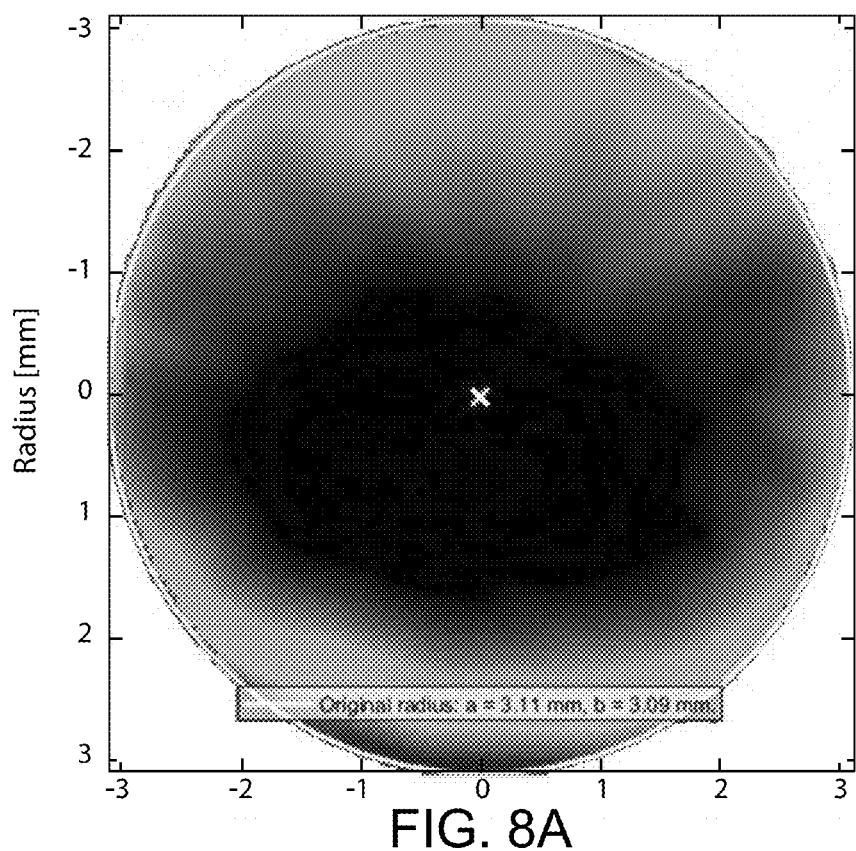
FIGS. 8A and 8B illustrate another method of documenting wavefront aberrations, illustrating the differences between the young and older patients in plots of wavefront aberrations in the plane of the pupil.
Figure 8B:
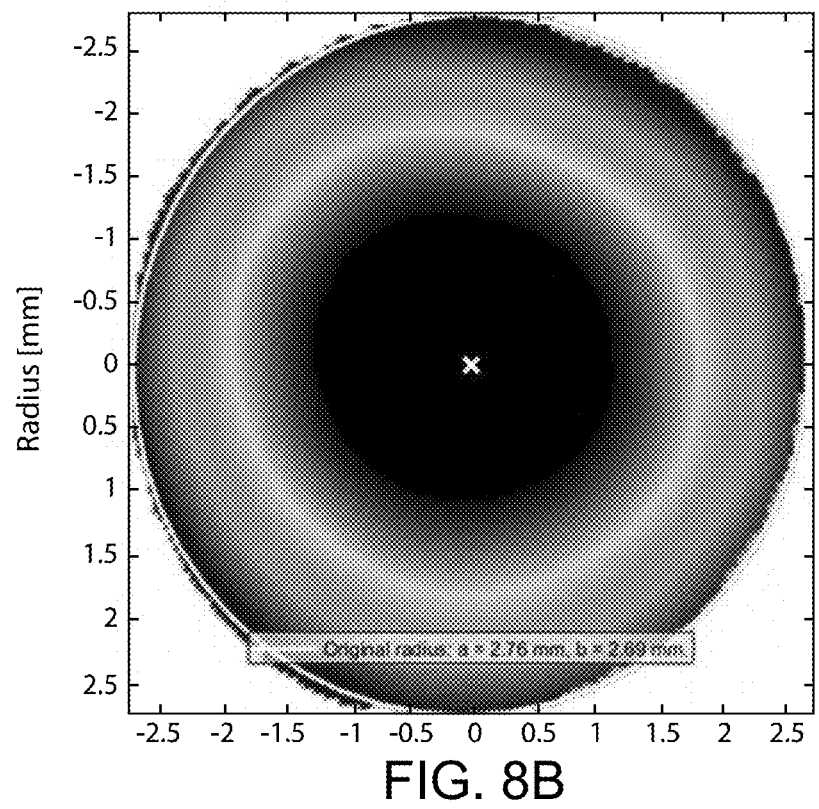

FIGS. 8A and 8B show another method of reporting out wavefront aberrations, illustrating the differences between the young patient (FIG. 8A) and older patient (FIG. 8B) in plots of wavefront aberrations in the plane of the pupil. The younger patient on top, i.e. 8A, has a wavefront that is fairly consistent across the pupil, but the older and more myopic patient on the bottom, i.e. 8B, has striking differences between the central and peripheral regions of the pupil.

Figure 9A:
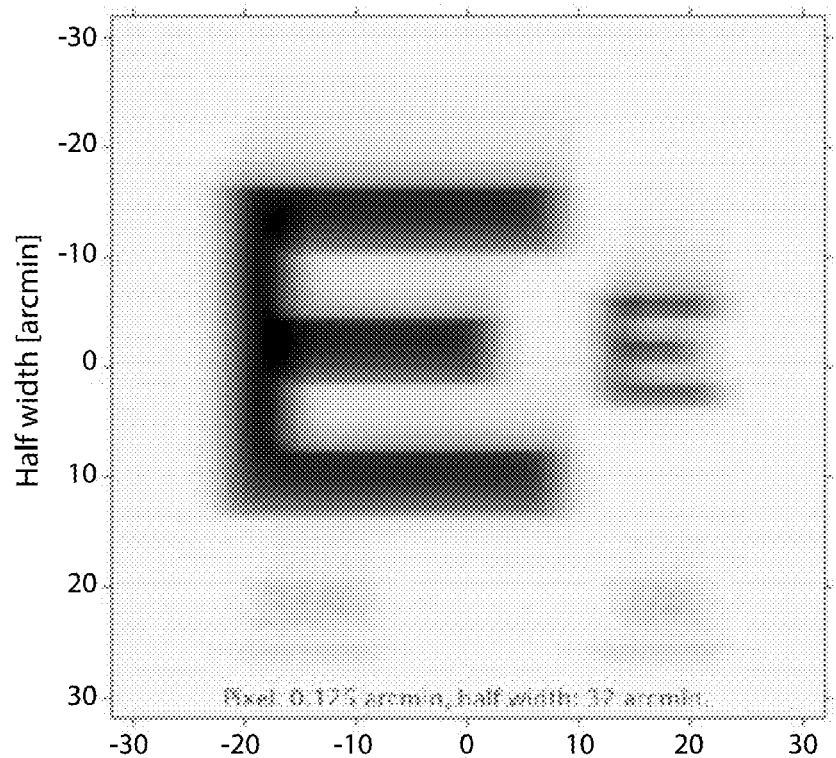
FIGS. 9A and 9B are representations of the expected degradation contrast of the letter E due to the wavefront aberrations, comparing a younger eye that is emmetropic with an older eye that is myopic.
Figure 9B:
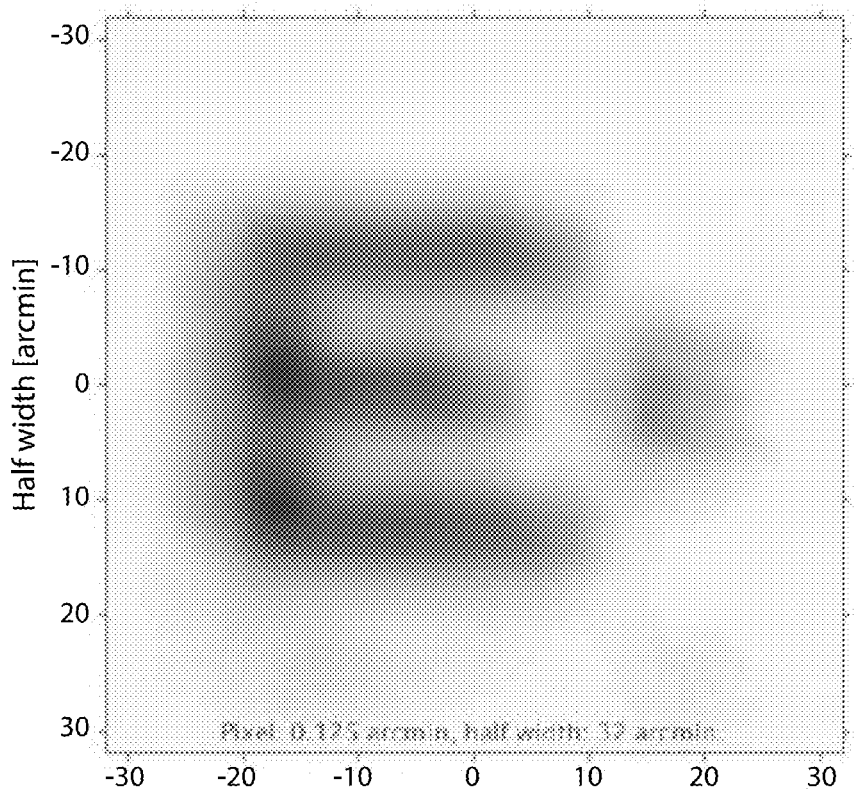

FIGS. 9A and 9B are representations of the expected degradation contrast of the letter E due to the wavefront aberrations, comparing the younger eye (FIG. 9A) that is emmetropic with the older eye (FIG. 9B) that is myopic and has increased higher order wavefront aberrations. The letter E is expected to be less sharply focused on the retina of the older patient and therefore a decrease in visual function is expected even if the retina is healthy. Again, this demonstrates that the pyramidal wavefront sensing method is used in one or more embodiments; i.e. the method of measuring wavefront aberrations is not limited to the Hartmann Shack method.

While an exemplary embodiment incorporating the principles of the present invention has been disclosed herein above, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A system to measure visual function of an eye having a pupil, while quantifying or minimizing factors that negatively affect vision but are unrelated to the status of the retina, comprising:
   (a) a visual display that projects light through the pupil of the eye and onto the retina, and having an optical design capable of passing the majority of the light through the pupil to eliminate individual differences in the amount of light reaching the retina while transmitting a visual stimulus accurately including at high spatial frequencies or low contrast;
   (b) a NIR or long visible wavelength imaging device to image the retina and subretinal structures and to provide detail about the status of the retina and locations of retinal structures;

(c) a processor to compare the visual stimulus from the visual display and the retinal image to provide the locus of the target on the retina, known as the locus of fixation and in other fields as the preferred retinal locus;

(d) wherein the processor determines from a sequence of retinal images, provided by the NIR or long visible wavelength imaging device, the variation of the locus of fixation over time;

(e) wherein the processor analyzes the retinal image based on image processing and reports the status of the retinal and subretinal structures at the locus of fixation according to imaging parameters;

(f) a wavefront measurement system to assess visual function being tested based on the deviations in the plane of the pupil of the eye of the wavefront for the light reaching the retina at the location of the visual stimulus;

(g) wherein the processor determines wavefront errors resulting from the optics of the eye from the wavefront measurements;

(h) a control mechanism to control one or more adaptive optics components to correct the wavefront errors of the visual display to achieve an improved focus of the visual stimulus on the retina;

(i) wherein the processor adjusts the focus of the visual stimulus on the retina based on the wavefront measurements and assesses corrected and uncorrectable wavefront aberrations;

(j) a response mechanism to record judgements about the visual stimulus;

(k) wherein the control mechanism controls one or more parameters of the visual stimulus of the visual wavelength display;

(l) wherein the processor computes the parameters to be used in the visual display or the final output, according to the results of b, c, d, e, g, i, and j.

2. The system of claim 1, wherein the light of the visual display is projected through a pupil of approximately 3 mm in diameter to provide sufficient numerical aperture to transmit high spatial frequency stimuli.

3. The system of claim 1, wherein the imaging device illuminates the retina by scanning the illumination across the retina or by projecting a series of illuminated regions onto the retina, with light from the retina detected in synchrony.

4. The system of claim 1, wherein the imaging device provides confocal imaging, and alternatively with the illumination beam and detection readout displaced in space or time, providing multiply scattered light imaging.

5. The system of claim 1, wherein the processor analyses images with detection offset with respect to illumination in two or more directions within an image or over time.

6. The system of claim 1, wherein the processor analyses images of different illumination wavelengths other than NIR or long wavelength visible illumination.

7. The system of claim 1, wherein the processor analyses a property of the light returning from the eye beyond only intensity, such as fluorescence, coherence, or polarization, either at each location or in aggregate over a wider area.

8. The system of claim 1, wherein the measurement device for the wavefront is a Hartmann-Shack sensor system.

9. The system of claim 1, wherein the measurement device for the wavefront uses long wavelength visible illumination or NIR illumination.

10. The system of claim 1, wherein the measurement device for the wavefront is devised to have sufficient resolution to allow specification of vision-impacting aberrations not limited to only sphere and cylinder, but of lower cost or less resolution than is required to control adaptive optics needed to produce diffraction limited imaging.

11. The system of claim 1, wherein the wavefront measurement system is temporally modulated to decrease the light needed for the measurements of wavefront aberrations, including but not limited to modulation of the illumination in synchrony with the sensor to improve signal to noise ratio.

12. The system of claim 1, wherein the wavefront measurement system has a separate illumination source from the visual display.

13. The system of claim 1, wherein the wavefront measurement device reports the wavefront aberrations for an approximately 3 mm pupil.

14. The system of claim 1, wherein the wavefront measurement device reports the wavefront aberrations for an approximately a 3 mm pupil and reports the amount corrected for sphere, cylinder, and specific other lower order aberrations.

15. The system of claim 1, wherein the wavefront measurement device reports the wavefront aberrations for an approximately a 3 mm pupil and reports the amount corrected by the adaptive optics for sphere, cylinder, other lower order aberrations, and higher order aberrations.

16. The system of claim 1, wherein the wavefront measurement device reports the wavefront aberrations for an approximately a 3 mm pupil and reports the amount corrected by the adaptive optics for sphere, cylinder, other lower order aberrations, and higher order aberrations in relation to clinical or other data concerning the anterior segment health, such as tear film and lens.

17. The system of claim 1, wherein the wavefront measurement device reports the wavefront aberrations for an approximately 3 mm pupil and reports the amount corrected by the adaptive optics for sphere, cylinder, other lower order aberrations, and higher order aberrations in relation to clinical or other data concerning the anterior segment health, such as tear film and lens to refine the measure central tendency and variability of the visual function measured.

18. The system of claim 1, wherein the focus on the retina from the visual display is improved by the adaptive optics, and the improvement is quantified by the measurements of the wavefront measurement system.

19. The system of claim 1, wherein the focus on the retina from the visual display is improved by the adaptive optics, and the control parameters of the adaptive optics are specified by ancillary measurements.

20. The system of claim 1, wherein the imaging device has a wide field of view, 8 to 60 degree visual angle to allow for eccentric fixation and determination of retinal landmarks.

21. The system of claim 1, wherein the imaging device has a magnified field of view, less than 8 degree visual angle.

22. The system of claim 1, wherein the measurement of visual function includes a database or model of the impact on the visual function of the wavefront aberrations that cannot be corrected.

23. The system of claim 1, wherein illumination of the wavefront measurement system is performed by the visual display.

24. The system of claim 1, but wherein the measurement of visual function includes a database or model of the impact on the visual function measurement central tendency and variability when any of the input measurements are not measured in the same device in a contemporaneous manner, and alternative or ancillary measurements are input, constrained to the set of: b, c, d, e, g, i, or j, the detection offset with respect to illumination in two or more directions within an image or over time, and images of different illumination wavelengths other than NIR or long wavelength visible illumination.

25. A method to measure visual function, while quantifying or minimizing factors that negatively affect vision but are unrelated to the status of the retina, comprising:
- a) projecting light through the pupil of the eye and onto the retina, and passing the majority of the light through the pupil to eliminate individual differences while transmitting a visual stimulus accurately including at high spatial frequencies or low contrast;
- (b) imaging the retina and subretinal structures with NIR or long visible wavelength light to provide details about the health of the retina and locations of retinal structures;
- (c) comparing the visual stimulus received from the visual display and the retinal image to provide the locus of the target on the retina, known as the locus of fixation and in other fields as the preferred retinal locus;
- (d) determining from a sequence of retinal images the variation of the locus of fixation over time, known as fixation stability;
- (e) analyzing the retinal image and reporting of the status of the retinal and subretinal structures at the locus of fixation according to imaging parameters;
- (f) measuring the wavefront aberrations to assess the deviations in the plane of the pupil of the eye of the wavefront for the light reaching the retina at the location of the visual stimulus;
- (g) determining the focus on the retina of the optics of the eye from the wavefront measurements;
- (h) correcting the wavefront errors of the visual display to achieve better focus of the visual stimulus on the retina;
- (i) reporting corrected and uncorrectable wavefront aberrations to an operator and using this information to interpret the visual function measurements;
- (j) recording judgements by the patient about the visual stimulus;
- (k) controlling one or more parameters of the visual stimulus based on the patient's response or a predetermined sequence;
- (l) computing the parameters to be used in the visual display or the final output, according to the results of b, c, d, e, g, i, and j, and a model of the visual function being measured including prior data, all working together to specify the visual function that could potentially be reached by a given eye, wherein the measurement quantifies factors negatively affecting vision that are unrelated to retinal status, and optimized to produce metrics of central tendency and variability that describe the status and potential status of the retina.

26. The method of claim 25, wherein the visual function include the expectation for vision with successful retinal treatment or if elimination of unrelated factors such as lens opacities achieved, wherein the visual function metrics include a measure of central tendency and variability, and specify an upper bound that must be exceeded to conclude that retinal status is being improved, and the visual function metrics include a lower bound that must be exceeded to conclude that retinal status is not worsening.

* * * * *